US012793824B2

(12) United States Patent
Sharma et al.

(10) Patent No.: US 12,793,824 B2
(45) Date of Patent: Nov. 10, 2026

(54) AUTOMATED INFORMATION EXTRACTION AND ENRICHMENT IN PATHOLOGY REPORT USING NATURAL LANGUAGE PROCESSING

(71) Applicant: Roche Molecular Systems, Inc., Pleasanton, CA (US)

(72) Inventors: Vishakha Sharma, Pleasanton, CA (US); Yogesh Pandit, Pleasanton, CA (US); Ram Balasubramanian, Pleasanton, CA (US)

(73) Assignee: Roche Molecular Systems, Inc., Pleasanton, CA (US)

(*) Notice: Subject to any disclaimer, the term of this patent is extended or adjusted under 35 U.S.C. 154(b) by 78 days.

(21) Appl. No.: 18/939,395

(22) Filed: Nov. 6, 2024

(65) Prior Publication Data

US 2025/0078971 A1 Mar. 6, 2025

Related U.S. Application Data

(63) Continuation of application No. 17/639,441, filed as application No. PCT/US2020/049738 on Sep. 8, 2020, now Pat. No. 12,170,133.

(Continued)

(51) Int. Cl.
*G16H 15/00* (2018.01)
*G06F 40/20* (2020.01)
(Continued)

(52) U.S. Cl.
CPC ............. *G16H 15/00* (2018.01); *G06F 40/20* (2020.01); *G06F 40/279* (2020.01); *G06V 30/30* (2022.01);
(Continued)

(58) Field of Classification Search
USPC ...................................... 705/2; 704/1–504, 9
See application file for complete search history.

(56) References Cited

U.S. PATENT DOCUMENTS 8,935,155 B2 * 1/2015 Bretschneider ....... G06F 40/216 704/9
10,395,772 B1 * 8/2019 Lucas .................. G06F 18/217
(Continued)

FOREIGN PATENT DOCUMENTS

CN 114341838 A * 4/2022 ............. G16H 30/20
JP 2015-505082 A 2/2015
(Continued)

OTHER PUBLICATIONS

Office Action in European Patent Application 20780426.1 mailed Apr. 15, 2025; 6 pages.
(Continued)

*Primary Examiner* — Marcus T Riley
(74) *Attorney, Agent, or Firm* — Kilpatrick Townsend & Stockton LLP

(57) ABSTRACT

In one example, a method being performed by a computer system comprises: receiving an image file containing a pathology report; performing an image recognition operation on the image file to extract input text strings; detecting, using a natural language processing (NLP) model, entities from the input text strings, each entity including a label and a value; extracting, using the NLP model, the values of the entities from the input text strings; converting, based on a mapping table that maps entities and values to pre-determined terminologies, the values of at least some of the entities to the corresponding pre-determined terminologies; and generating a post-processed pathology report including the entities detected from the input text strings and the corresponding pre-determined terminologies.

20 Claims, 18 Drawing Sheets

Related U.S. Application Data

(60) Provisional application No. 62/897,252, filed on Sep. 6, 2019.

(51) Int. Cl.

| | |
|---|---|
| ***G06F 40/279*** | (2020.01) |
| ***G06V 30/30*** | (2022.01) |
| ***G06V 30/416*** | (2022.01) |
| ***G16H 10/60*** | (2018.01) |
| ***G16H 30/20*** | (2018.01) |

(52) U.S. Cl.

CPC .......... *G06V 30/416* (2022.01); *G16H 10/60* (2018.01); *G16H 30/20* (2018.01)

(56) References Cited

U.S. PATENT DOCUMENTS

| | | | | |
|---|---|---|---|---|
| 10,957,433 | B2 * | 3/2021 | Lucas | G16H 10/60 |
| 11,089,052 | B2 * | 8/2021 | Epstein | G06F 16/951 |
| 11,537,643 | B2 * | 12/2022 | Duke | G06F 16/3323 |
| 11,594,222 | B2 * | 2/2023 | Lefkofsky | G06F 3/167 |
| 11,599,707 | B2 * | 3/2023 | Simpson | G06F 3/0484 |
| 11,610,667 | B2 * | 3/2023 | Gurson | G06N 3/045 |
| 11,615,890 | B2 * | 3/2023 | Chang | G16H 50/70<br>705/3 |
| 11,742,064 | B2 * | 8/2023 | Ozeran | G16H 10/20<br>705/3 |
| 11,810,654 | B2 * | 11/2023 | Chang | G16H 10/60 |
| 11,816,176 | B2 * | 11/2023 | Locker | G06F 16/958 |
| 11,836,997 | B2 * | 12/2023 | Swisher | G06F 40/10 |
| 11,915,809 | B2 * | 2/2024 | Chang | G16H 15/00 |
| 12,170,133 | B2 * | 12/2024 | Sharma | G06F 40/20 |
| 2018/0060533 | A1 * | 3/2018 | Reicher | G16H 10/60 |
| 2018/0239826 | A1 * | 8/2018 | Epstein | G06F 16/951 |
| 2020/0126663 | A1 * | 4/2020 | Lucas | G06F 18/217 |
| 2021/0090694 | A1 * | 3/2021 | Colley | G16H 10/40 |
| 2021/0210184 | A1 * | 7/2021 | Lucas | G06F 40/274 |
| 2022/0301670 | A1 * | 9/2022 | Sharma | G06F 40/20 |
| 2024/0021280 | A1 * | 1/2024 | Barnard | G16H 10/40 |
| 2025/0078971 | A1 * | 3/2025 | Sharma | G16H 15/00 |

FOREIGN PATENT DOCUMENTS

| | | | | | |
|---|---|---|---|---|---|
| JP | 2017-513590 | A | | 6/2017 | |
| JP | 2019-049964 | A | | 3/2019 | |
| JP | 2022546593 | A | * | 11/2022 | G16H 10/60 |
| JP | 7392120 | B2 | * | 12/2023 | G06F 40/279 |
| JP | 2024012659 | A | * | 1/2024 | G06F 40/279 |
| JP | 2024503532 | A | * | 1/2024 | G16H 40/60 |
| WO | 2015/159182 | A1 | | 10/2015 | |
| WO | WO-2021046536 | A1 | * | 3/2021 | G16H 30/20 |

OTHER PUBLICATIONS

International Search Report and Written Opinion in PCT/US2020/049738 mailed Dec. 21, 2020; 11 pages.

Office Action in Japanese Patent Application 2022-514669 mailed Jun. 20, 2023; 9 pages.

Office Action in Chinese Appln. 202080062284.0 mailed May 20, 2024; 10 pages.

Office Action in Japanese Patent Application 2023-197189 mailed Jan. 7, 2025; 6 pages.

* cited by examiner

200

| Medial Entities | Value |
| --- | --- |
| Specimen laterality | Right |
| Tumor site | Middle lobe |
| Tumor size | 5.3 x 4.0 x 3.0 cm |
| Histology | Squamous Carcinoma |
| Histology grade | Well to moderately differentiated keratinizing squamous cell carcinoma |
| Regional Lymph Nodes/ Category (pN) | N2 |
| Primary tumor (pT) | pT3 |
| Overall grade | G2 |

210

FIG. 2A

250

<table>
<tr><th>Entity</th><th>Value</th><th>SNOMED Concept (Concept ID)</th></tr>
<tr><td>Histology</td><td>Squamous Carcinoma</td><td>59529006 | Squamous cell carcinoma in situ</td></tr>
<tr><td>Tumor Site</td><td>Lower Lobe</td><td>90572001 | Structure of lower lobe of lung (body structure)</td></tr>
<tr><td>Specimen Laterality</td><td>Left</td><td>44029006| Left lung structure (body structure)</td></tr>
</table>

FIG. 2B

530

| label | tp | fp | fn | prec | rec | f1 |
|---|---|---|---|---|---|---|
| I-Grade | 327 | 13 | 13 | 0.9617647 | 0.9617647 | 0.9617647 |
| B-Grade | 462 | 17 | 11 | 0.96450937 | 0.9767442 | 0.9705882 |
| B-pN | 180 | 3 | 9 | 0.9836066 | 0.95238096 | 0.96774197 |
| I-pT | 18 | 2 | 6 | 0.9 | 0.75 | 0.81818175 |
| B-Procedure | 352 | 71 | 52 | 0.8321513 | 0.8712871 | 0.85126966 |
| I-Margins | 24 | 55 | 16 | 0.30379745 | 0.6 | 0.40336132 |
| B-Laterality | 552 | 75 | 40 | 0.8803828 | 0.9324324 | 0.9056604 |
| I-Tests | 180 | 5 | 17 | 0.972973 | 0.9137056 | 0.9424084 |
| I-pM | 31 | 5 | 6 | 0.8611111 | 0.8378378 | 0.84931505 |
| I-Laterality | 16 | 0 | 11 | 1.0 | 0.5925926 | 0.74418604 |
| B-Results | 237 | 22 | 30 | 0.9150579 | 0.8876405 | 0.9011407 |
| I-Localization | 477 | 117 | 99 | 0.8030303 | 0.828125 | 0.8153847 |
| B-Localization | 904 | 151 | 190 | 0.856872 | 0.8263254 | 0.8413215 |
| I-Results | 55 | 9 | 40 | 0.859375 | 0.57894737 | 0.69182396 |
| B-Positive | 187 | 75 | 17 | 0.71374047 | 0.9166667 | 0.8025752 |
| I-Size | 847 | 159 | 56 | 0.84194833 | 0.93798447 | 0.88737565 |
| B-Type | 770 | 92 | 97 | 0.89327145 | 0.88811994 | 0.89068824 |
| B-Extension | 73 | 44 | 49 | 0.62393165 | 0.59836066 | 0.61087865 |
| B-Examined | 99 | 16 | 19 | 0.8608696 | 0.83898306 | 0.8497854 |
| I-Procedure | 255 | 119 | 64 | 0.6818182 | 0.79937303 | 0.7359308 |
| B-pM | 84 | 8 | 4 | 0.9130435 | 0.95454544 | 0.9333333 |
| I-Examined | 16 | 1 | 2 | 0.9411765 | 0.8888889 | 0.9142857 |
| I-Type | 308 | 24 | 43 | 0.92771083 | 0.8774929 | 0.9019034 |
| B-Margins | 184 | 81 | 16 | 0.69433963 | 0.92 | 0.79139787 |
| B-Tests | 495 | 45 | 55 | 0.9166667 | 0.9 | 0.9082569 |
| I-Extension | 307 | 176 | 18 | 0.63692945 | 0.94461536 | 0.76084256 |
| B-Size | 517 | 41 | 82 | 0.92652327 | 0.8631052 | 0.8936905 |
| I-Positive | 6 | 3 | 1 | 0.6666667 | 0.85714287 | 0.75 |
| B-pT | 219 | 9 | 7 | 0.9605263 | 0.96902657 | 0.9647577 |
| I-pN | 50 | 5 | 3 | 0.90909094 | 0.9433962 | 0.92592597 |

tp: 8232 fp: 1442 fn: 1073 labels: 30

Macro-average prec: 0.8400961, rec: 0.8535829, f1: 0.8467858

Macro-average prec: 0.85094064, rec: 0.88468564, f1: 0.8467851

FIG. 5E

AUTOMATED INFORMATION EXTRACTION AND ENRICHMENT IN PATHOLOGY REPORT USING NATURAL LANGUAGE PROCESSING

CROSS-REFERENCES TO RELATED APPLICATIONS

The present application is a continuation of U.S. patent application Ser. No. 17/639,441 filed Mar. 1, 2022, which is a U.S. National Phase Application Under 371 of PCT/US2020/049738 filed Sep. 8, 2020, which claims benefit of priority to U.S. Provisional Patent Application No. 62/897,252, filed Sep. 6, 2019, the contents of which are herein incorporated by reference in their entireties for all purposes.

BACKGROUND

Every day, hospitals create a tremendous amount of clinical data across the globe. Medical personnel, such as clinicians and clinician staff, need to analyze the clinical data to administer care to the patients. Analysis of this data is also critical in providing detailed insights in healthcare delivery and quality of care, as well as providing a basis to improve healthcare.

Unfortunately, a large proportion of the clinical data is difficult to access and analyze, since most data are either in paper form or in the form of scanned images. The data may include, for example, pathology reports or any other data that are neither associated with a structured data model nor organized in a pre-defined manner to define the context and/or meaning of the data. Because of the physical form of the data, as well as the fact that the data are unstructured, clinicians and clinical staff typically need to spend a lot of time in reading through a pathology report of a patient to obtain important clinical data, such as diagnosis, treatment history, etc., and the time will add up for reading the pathology reports of a large number of patients. Moreover, manual extraction is also laborious, slow, costly, and error-prone. The manual processing and extraction of clinical data from pathology reports can pose a huge burden on the medical personnel and affect their abilities in administering care to the patients. Large scale manual processing of pathology reports to provide detailed insights in healthcare delivery and quality of care is also not feasible due to expense and time limitations.

BRIEF SUMMARY

Disclosed herein are techniques for automated information extraction and enrichment in pathology reports. The pathology reports can include electronic reports from various primary sources (e.g., at one or more healthcare institutions) including, for example, an EMR (electronic medical record) database, a PACS (picture archiving and communication system), a Digital Pathology (DP) system, an LIS (laboratory information system) including genomic data, an RIS (radiology information system), patient reported outcomes database, wearable and/or digital technologies, and social media. The pathology reports can also be in paper form and originate from the clinician/clinician staff. The pathology reports can be in the form of image files (e.g., Portable Document Format (pdf), bitmap image file (BMP file)) obtained by scanning the paper-form pathology reports.

In some examples, a workflow is provided to extract pathology entities from images of pathology reports. The workflow can begin with extracting text strings from an image file of a pathology report. The extraction of the text strings from the image file can be based on an image recognition process to recognize characters and/or text strings from the image, such as optical character recognition (OCR), optical word recognition, etc. The workflow can further include recognizing, using a natural language processor (NLP), entities from the input text strings, each entity including a label and a value, and determining the values of the entities from the text strings. The entities can generally refer to pre-defined medical categories and classifications, such as medical diagnoses, procedures, medications, specific locations/organs in the patient's body, etc. Each entity can have a label that indicates the category/classification, and a value corresponding to the data being categorized/classified. In some examples, the workflow further includes mapping the values of at least some of the entities to standard terminologies, such as clinical terminologies and codes defined under the Systematized Nomenclature of Medicine (SNOMED) standard. The workflow can then generate structured medical data that associate labels of the entities with at least one of the values of the entities or the standardized terminologies based on the mapping.

The structured medical data can be provided for various applications. For example, the structured medical data can be stored in a searchable database from which the entities and their values (standardized or not) can be retrieved based on search queries. The searchable database, as well as the structured medical data, can also be made available to various applications, such as a clinical decision support application, an analytics application, etc., for processing. For example, the clinical decision support application can retrieve entities relevant to a clinical decision (e.g., diagnosis, procedure history, medication history) and their values from the database, and process the entities to generate an output to support a clinical decision. An analytics application can obtain entities related to, for example, treatment history and diagnosis from the pathology reports of a large number of patients and perform analysis to obtain insights in healthcare delivery and quality of care. In other examples, a clinical portal application can be provided to display the structured medical data, and/or to display an image of a pathology report with extracted entity information overlaid on the image.

The NLP model can be trained to identify sequences of text strings, including entities and values, and extract the entities and values based on the identification. The NLP can be trained in a two-step process. As a first step, the NLP model can be trained based on documents including common medical terminologies to build a baseline NLP sub-model. As a second step, the baseline NLP sub-model can then be trained using text strings from pathology reports, to expand the model to include specific pathology terminologies. The second step of the training operation can be performed using CoNLL (Conference on Natural Language Learning) files.

In addition, various techniques can determine the various parameters of the image recognition operation for improving the extraction accuracy of the NLP. In some examples, a parameter sweeping operation can be performed to obtain different combinations of values of the parameters. The image recognition operation can then be performed iteratively, with each iteration performed based on a combination of values of the parameters. The text recognition accuracy for each iteration can then be measured, and a particular combination of parameters' values that lead to the highest text recognition accuracy can be used to configure the image recognition operation for the workflow. As another example, the determination of the parameters of the image recognition operation can be based on the NLP output. Specifically, the image recognition operation can be pre-configured based on a first set of parameters values. The pre-configured image recognition operation can be performed on images of pathology reports to extract text strings, and the text strings can be input to the NLP to extract pathology entities. The parameters of the image recognition operation can then be adjusted based on the accuracy of extraction by the NLP.

These and other embodiments of the invention are described in detail below. For example, other embodiments are directed to systems, devices, and computer-readable media associated with methods described herein.

A better understanding of the nature and advantages of embodiments of the present invention may be gained with reference to the following detailed description and the accompanying drawings.

BRIEF DESCRIPTION OF THE DRAWINGS

The detailed description is set forth with reference to the accompanying figures.

FIG. 2A and FIG. 2B illustrate examples of post-processing of a conventional pathology report that can be implemented by examples of the present disclosure.

FIG. 5A, FIG. 5B, FIG. 5C, FIG. 5D, and FIG. 5E illustrate examples of a training operation of a natural language processing model of the system of FIG. 3.

DETAILED DESCRIPTION

Figure 1:
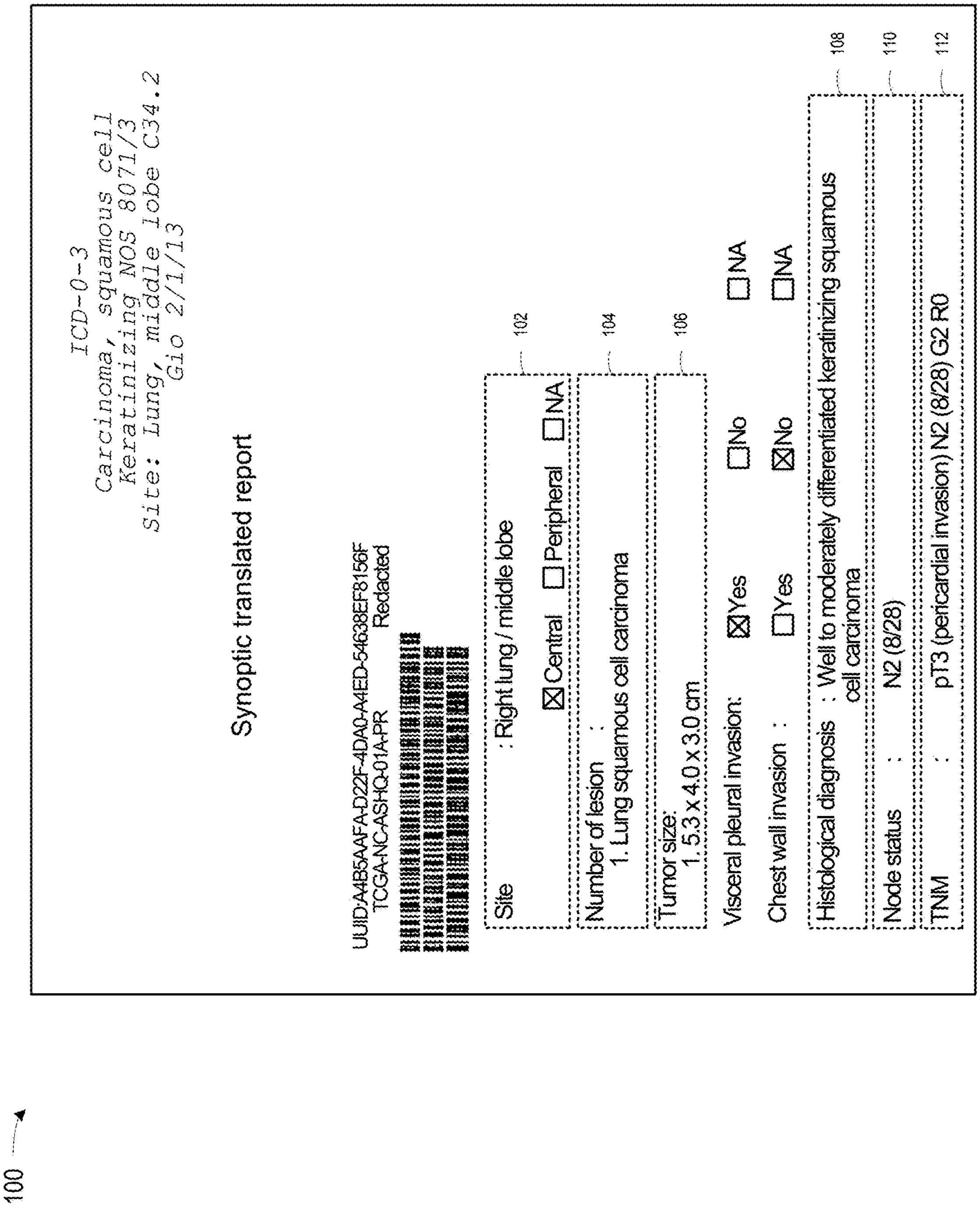
FIG. 1 illustrates an example of a conventional pathology report.

Disclosed herein are techniques for automated information extraction and enrichment in pathology reports. The pathology reports can originate from electronic reports from various primary sources (at one or more healthcare institutions) including, for example, an EMR (electronic medical record) database, a PACS (picture archiving and communication system), a Digital Pathology (DP) system, an LIS (laboratory information system) including genomic data, an RIS (radiology information system), patient reported outcomes database, wearable and/or digital technologies, and social media. The pathology reports can also be in paper form and originate from the clinician/clinician staff. The pathology reports can be in the form of image files (e.g., Portable Document Format (pdf), bitmap image file (BMP file)) obtained by scanning the paper-form pathology reports.

In some embodiments, a workflow is provided to extract pathology entities from images of pathology reports. The workflow can begin with extracting text strings from an image file of a pathology report. The extraction of the text strings from the image file can be based on an image recognition process to recognize characters and/or text strings from the image, such as optical character recognition (OCR), optical word recognition, etc. The workflow further includes recognizing, using a natural language processor (NLP), entities from the text strings, each entity including a label and a value, and determining the values of the entities from the text strings. The entities generally refer to predefined medical categories and classifications, such as medical diagnoses, procedures, medications, specific locations/organs in the patient's body, etc. Each entity has a label which indicates the category/classification, and a value which indicates the data being categorized/classified. In some examples, the workflow includes mapping the values of at least some of the entities to standard terminologies. The mapping can be part of an enrichment process, in which the values of at least some of the entities, which may be non-standardized representation of the categorized/classified data, are converted into standardized data, such as clinical terminologies and codes defined under the Systematized Nomenclature of Medicine (SNOMED) standard. The workflow can then generate structured medical data that associate the labels of the entities with at least one of the values of the entities or the standardized terminologies.

The structured medical data can be provided for various applications. For example, the structured medical data can be stored in searchable database from which the entities and their values (standardized or not) can be retrieved based on search queries. The searchable database, as well as the structured medical data, can also be made available to various applications, such as a clinical decision support application, an analytics application, etc., for processing. For example, the clinical decision support application can retrieve entities relevant to a clinical decision (e.g., diagnosis, procedure history, medication history) and their values from the database, and process the entities to generate an output to support a clinical decision. An analytics application can obtain entities related to, for example, treatment history and diagnosis from the pathology reports of a large number of patients and perform analysis to obtain insights in healthcare delivery and quality of care.

As another example, a clinical portal application can be provided which implements an end-to-end enrichment workflow operation. The clinical portal application can receive an image of a pathology report from a patient database, and perform an optical character recognition (OCR) operation on the image to generate first data including the extracted text strings and their image locations in the image. The clinical portal application can then use the NLP to extract pathology entities (including labels and values) from the extracted text strings. The clinical portal application can then assemble the entities into structured medical data and store the structured medical data back to the patients database. The clinical portal application can also display the structured medical data. In some examples, the clinical portal application can display the structured medical data in a structured form (e.g., in the form of tables, populated forms) to enable a user of the portal (e.g., clinician, clinician staff) to efficiently identify the medical information they look for. In some examples, the clinical portal application can include a display interface to display the image, as well as selectable highlight marking overlaid on the text strings which the NLP determines to represent pathology entities. The display interface can also detect a selection of the highlight marking over a set of text strings and display a pop up window including the entity label and value, as well as other enrichment information (e.g., standardized data based on SNOMED) of the selected text strings.

The NLP model can be trained to identify sequences of text strings including entities and values, and extract the entities and values based on the identification. The NLP can be trained in a two-step process. As a first step, the NLP model can be trained based on documents including common medical terminologies to build a baseline NLP sub-model. The baseline NLP sub-model can be used to provide a primary context for identifying sequences of text strings that include common medical terminologies that may (or may not) include pathology entities. The baseline NLP model sub-can be trained/built based on biomedical articles from various major sources such as, for example, PubMed Central®, a free full-text archive of biomedical and life sciences journal literature at the U.S. National Institutes of Health's National Library of Medicine. As a second step, the baseline NLP sub-model is then trained using text strings from pathology reports, to expand the sub-model to include pathology entities. The second step of the training operation can be performed using CoNLL (Conference on Natural Language Learning) files. A CoNLL file may include text strings extracted from other pathology reports, with each text tagged with either an entity label or an indication of being a non-entity. The NLP can be trained based on the CoNLL files from multiple pathology reports. In some examples, the training can be specific for a hospital, a clinical group, or an individual clinician, such that an NLP can be trained to learn the preference of words of the hospital/clinical group/clinician, which can maximize the accuracy of extraction of entities and their values. In some embodiments, statistics of the accuracies of extraction of entities can be maintained. If the statistics indicate that the NLP has a low extraction accuracy when extracting the entities from the input text strings, the input text strings can be tagged to generate a new CoNLL file, and the NLP can be retrained using the new CoNLL file to improve the extraction accuracy.

In addition, various techniques are proposed to determine the various parameters of the image recognition operation to improve the extraction accuracy of the NLP. The parameters may include, for example, an erosion value, a page iterator level, a page segmentation mode, or a scaling factor. The erosion value can indicate whether a blurred lines smoothing operation is performed. The page iterator level can refer to a granularity of the image recognition operation—whether it is performed by treating the entire page as a block or treating sections within a page (a paragraph, a line, a word, a character, etc.) as blocks to increase the granularity of the image recognition operation. The page segmentation mode can detect a slanted orientation of the page being processed and adjust the image recognition operation to correct for the slanted orientation. The scaling factor can set a zoom level to zoom into or zoom out of the image to be processed.

In some examples, a parameter sweeping operation can be performed to obtain different combinations of values of the parameters. The image recognition operation can then be performed iteratively on a set pathology reports, with each iteration performed based on a combination of values of the parameters. The text recognition accuracy for each iteration can then be measured, and a particular combination of parameters' values that lead to the highest text recognition accuracy can be used to configure the image recognition operation for the workflow.

As another example, the determination of the parameters of the image recognition operation can be based on the NLP output. Specifically, the image recognition operation can be pre-configured based on a first set of parameters values. The pre-configured image recognition operation can be performed on images of pathology reports to extract text strings, and the text strings can be input to the NLP to extract pathology entities. The parameters of the image recognition operation can then be adjusted based on the accuracy of extraction by the NLP.

Tuning the parameters of the image recognition operation based on the NLP output can be advantageous, especially in a case where the image file contain notes by a particular physician, which may include non-standard codes and phrases. If the OCR outputs are compared against standardized phrases to determine the text recognition accuracy, the comparison may lead to incorrect conclusions about the text recognition accuracy for a particular set of OCR parameters when the text strings contain non-standard codes and phrases. On the other hand, as the NLP model has been trained to recognize non-standard codes and phrases, as well as standardized terminologies, using the NLP output to determine the text recognition accuracy can ensure that the text recognition accuracy measurement is less affected by the presence of non-standard codes and phrases in the OCR output.

The disclosed techniques can enable an automated workflow that starts by processing images of pathology reports to extract text strings, followed by extraction of entities and their values from the text strings using NLP, enrichment of the extracted entities and values by mapping them to standard terminologies, and generation of structured medical data containing the extracted entities and at least one of the extracted values or standard terminologies. Compared with a case where clinicians and clinical staff need to manually read through a pathology report to extract the relevant information, the disclosed techniques can substantially expedite the extraction process and reduce the time/resources the clinicians and clinical staff need to obtain the needed information from the pathology reports, which in turn allow them to allocate more time/resources in finding the right treatments and administering the treatments to the patient. Moreover, by making the structured medical data accessible by other applications, such as clinical support applications, analytics applications, etc., a large scale analysis of pathology reports of a large patient population can be performed to provide insights in healthcare delivery and quality of care, to provide relevant data to support a clinical decision made by a clinician, etc. With the improvements in the overall speed of data flow and in the correctness and completeness of extraction of medical data, wider and faster access of high-quality patient data can be provided for clinical and research purposes, which can facilitate the development in treatments and medical technologies, as well as the improvement of the quality of care provided to the patients.

I. EXAMPLES OF INFORMATION EXTRACTION AND ENRICHMENT FROM PATHOLOGY REPORTS

FIG. 1 illustrates an example of a conventional pathology report 100. A pathology report is a medical document written by a pathologist and can provide a histological diagnosis based on the pathologist's examination of a sample of tissue taken from the patient's tumor. From the tumor tissue, the pathologist can find out, for example, whether the issue is cancerous or non-cancerous, and other specific details about the tumor's features. All this information can be part of the pathology report. Based on these information, a treatment can be formulated.

Referring to FIG. 1, pathology report 100 may include multiple sections of the diagnosis information. For example, pathology report 100 may include, among other things, a section 102 indicating a location of the tumor (e.g., right lung/middle lobe), a section 104 indicating a number of lesions (e.g., lung squamous cell carcinoma), a section 106 indicating the tumor size (e.g., 5.3×4.0×3.0 cm), a section 108 indicating the histological diagnosis (e.g., well to moderately differentiated keratinizing squamous cell carcinoma), a section 110 indicating a node status (e.g., N2 (8/28)), and a section 112 indicating TNM (tumor nodes metastasis) staging (e.g., pT3 (pericardial invasion) N2 (8/28) G2 R0). Pathology report 100 can be in the paper form, or stored as an image file (e.g., a pdf file, a BMP file) generated by scanning a page containing pathology report 100.

A clinician and/or a clinician staff member can read through pathology report 100 and manually extract the medical information they are looking for. Such arrangements, however, can be laborious, slow, costly, and error-prone. Specifically, the pathology reports may not be organized in a uniform format and structure, especially for reports generated from different hospitals and groups. As a result, the reader may need to read through the entire pathology report 100 to search for certain medical information, which can be very time-consuming and laborious, especially when the reader needs to read through a large volume of pathology reports of a large patient population.

The manual extraction process can also be error-prone. One source of error can be attributed to the laborious extraction process, since the reader may have only a very limited amount of time to read through the pathology report to find the information he or she needs, and the reader may make mistakes in reading and/or transcribing the information obtained from the pathology report. Another source of error can be attributed to the fact that different clinicians may have different ways of documenting the diagnosis results, which can cause confusion and incorrect interpretations. For example, for section 110, the reader may have difficulty understanding the meaning of "node status" and the associated value "N2 8/28." As a result, the reader may have an incorrect interpretation of section 110. Another source of error could be mapping key entities to standard terminology. Standard terminology by default may have a lot of redundancy, and just looking it up may not help resolve an extracted entity to a normalized term. For example, the word "lung" may be associated with more than 20 normalized concepts. Identifying the concept the word "lung" maps to can be challenging to do manually.

FIG. 2A and FIG. 2B illustrate example results of post-processing pathology report 100 which can be implemented by techniques of the present disclosure. As shown in FIG. 2A, the diagnosis information in sections 102-112 of pathology report 100 can be mapped to various medical entities. A medical entity can refer to a pre-defined medical category and classification. The medical entities may include, for example, medical diagnoses, procedures, medications, and specific locations/organs in the patient's body. A medical entity can be defined based on a universal standard, such as SNOMED, such that every clinician and health care provider attach the same meaning to that medical entity. A list of medical entities of a typical pathology report, and their meanings, can be as follows:

TABLE 1

| Entities | Meaning |
|---|---|
| Diagnosis | Process of identifying a disease, condition, or injury from its signs and symptoms |
| Procedure | Surgical procedure(s) through which the histological samples were obtained |
| Specimen Laterality | The side of the body where a breast or lung primary invasive tumor is localized (e.g., Left or Right) |
| Tumor Site | A primary tumor is a tumor growing at the anatomical site where tumor progression began and proceeded to yield a cancerous mass. Most cancers develop at their primary site but then go on to metastasize or spread to other parts of the body. These further tumors are secondary tumors. |
| Size of Invasive Carcinoma | Length x Width x Height |
| Histologic Type | Histological type for a primary invasive tumor (words indicating the fact that the tumor is invasive are also labeled) |
| Histologic Grade | A description of a tumor based on how abnormal the cancer cells and tissue look under a microscope and how quickly the cancer cells are likely to grow and spread. |
| Overall Grade | Number of primary invasive tumor foci (tumors) |
| Tumor Focality | Nuclear pleomorphism degree of a breast primary invasive tumor |
| Nuclear Grade | Extension of a primary invasive tumor at colonic wall level or indicating direct extension to adjacent organs |
| Tumor Extension | All surgical margins status for a primary invasive tumor (with or without tumoral cells) |
| Margins | Presence or absence of in situ malignant lesions (DCIS or LCIS) at the level of a surgical margin |
| Margins, DCIS Carcinoma margins | Colon proximal surgical margin status of a primary invasive tumor (with or without tumoral cells) |
| Margins, Proximal | Colon distal surgical margin status of a primary invasive tumor (with or without tumoral cells) |
| Margins, Distal | Colon radial/mesenteric surgical margin status of a primary invasive tumor (with or without tumoral cells) |
| Margins, radial or mesenteric | A surgical margin, other than the ones included in the attributes list, or its status for a primary invasive tumor (with or without tumoral cells) |
| Margin, other | Bronchial surgical margin(s) status for a primary invasive tumor (with or without tumoral cells) |
| Margins, bronchial | Vascular surgical margin(s) status for a primary invasive tumor (with or without tumoral cells) |
| Margins, vascular | Parenchymal surgical margins status for a primary invasive tumor (with or without tumoral cells) |

TABLE 1-continued

| Entities | Meaning |
|---|---|
| Margins, parenchymal | Numeric |
| Number of Lymph Nodes involved by Tumor | Numeric |
| Number of Lymph Nodes Examined | Tumor staging category |
| Primary Tumor (pT) | Lymph nodes staging category |
| Regional Lymph Nodes/ Category (pN) | Presence of distal metastasis in other organs or tissues (other than regional lymph nodes) |
| Distant Metastasis (pM) | Name of the biomarker test or biomarker analyzed |
| Biomarker Tests Performed | Status of the biomarkers analyzed (negative or positive) |
| Biomarker Tests Results | Process of identifying a disease, condition, or injury from its signs and symptoms |

Referring to FIG. 2A, the diagnosis information in sections 102-112 of pathology report 100 can be mapped to various medical entities of Table 1 to generate a digital pathology report 200 containing structured data organized based on the medical entities. For example, the information of section 102 can be split and mapped to both the entity "specimen laterality" (with a value "right") and the entity "tumor site" (with a value "middle lobe"). The information of section 104 can be mapped to an entity "histology" with a value "squamous carcinoma". The information of section 106 can be mapped to the entity tumor size with a value "5.3×4.0×3.0 cm". The information of section 108 can be mapped to the entity "histology grade" with a value "well to moderately differentiated keratinizing squamous cell carcinoma". The information of section 110 can be mapped to the entity "regional lymph nodes/category (pN)" with a value N2, whereas the information of section 112 can be split and mapped to the entity "primary tumor (pT)" (with a value pT3) and the entity "overall grade" (with a value G2). As each medical entity of digital pathology report 200 is defined based on a universal standard and has a well-defined meaning, the risk of the reader misinterpreting the meaning of the medical entity and its associated value can be reduced.

In some examples, digital pathology report 200 can be a plain text file in which the entities and the associated values are stored in the form of text strings and can be readily parsed/searched by other applications. Moreover, the arrangement of the entities and their associated values in digital pathology report 200 can be structured and follow a standardized order, such that each entity has its own pre-determined location in digital pathology report 200. With such arrangements, an application (or a human reader familiar with the standardized order) can look up a specific entity and its value in pathology report 200 based on the pre-determined location of the entity rather than searching through the entire pathology report to look for the entity, which can substantially speed up the extraction of medical information from digital pathology report 200.

As part of an enrichment process, a combination of an entity and a value of digital pathology report 200 can be mapped to pre-determined medical terminology defined based on a universal standard, such as SNOMED. Such arrangements allow the diagnosis result represented by a combination of entity and value to be according to the universal standard, which can further reduce the risk of misinterpretation and ambiguity. For example, referring back to FIG. 2A, section 210 indicates that the histology tumor site has a value "middle lobe" but the organ is not specified, which can create ambiguity and potential confusion about the exact location of the tumor site. But if section 210 is converted to a standardized and/universally-accepted form, the ambiguity/confusion about the exact location of the tumor site can be avoided.

FIG. 2B illustrates a mapping table 250, which illustrates examples of mapping between a pair of entity and value and a SNOMED concept, which can eliminate the risk of misinterpretation and ambiguity. For example, the entity "histology" with a value of "squamous carcinoma" can be mapped to the SNOMED concept "squamous cell carcinoma in situ" with a concept ID 59529006. Moreover, the entity "tumor site" with a value "lower lobe" can be mapped to the SNOMED concept "structure of lower lobe of lung" with a concept ID 90572001. Such mapping can be based on the pairing between the entity "tumor site" and value "lower lobe" as well information contained in section 102 which are not part of the entities but are extracted as context information, such as the text "lung". Similarly, the entity "specimen laterality" with a value "left" can be mapped to the SNOMED concept "left lung structure" with a concept ID 44029006, also based on the entity-value pairing as well as the context information. In all these cases, the SNOMED concept can clarify the exact tumor site locations to remove potential confusion/ambiguity.

As part of the enrichment process, each entity-value pair of digital pathology report 200 that maps (matches) to a SNOMED concept can be replaced with the SNOMED concept. For example, the entity-value pair in section 210 (tumor site—lower lobe) can be replaced with the SNOMED concept "structure of lower lobe of lung" and/or the SNOMED concept ID 90572001. On the other hand, entity-value pairs in digital pathology report 200 that do not have corresponding SNOMED concepts are not replaced. If there is no match, then the report can include the entity-value pair. The NLP can be trained to provide a SNOMED concept where applicable.

The replacement of an entity-value pair with its SNOMED concept can enrich digital pathology report 200 by including standard terminologies in the report, which can reduce the risk of misinterpretation and ambiguity associated with non-standard values of entities for a human reader. In some examples, the entity-value pairs of digital pathology report 200 can also be replaced with SNOMED concept IDs to reduce the data size of digital pathology report 200. Such arrangements can also facilitate processing of digital pathology report 200 by an application. Specifically, since an entity-value pair may have multiple alternative versions of values representing the same concept, an application that extracts and interprets an entity-value pair needs to have built-in capabilities to recognize the multiple alternative versions of the values to recognize the associated concept. On the other hand, an application can parse a SNOMED concept ID and link a concept with the concept ID unambiguously, which can reduce the complexity of the application.

II. A PATHOLOGY ENTITY EXTRACTION AND ENRICHMENT SYSTEM

As discussed above, a conventional pathology report, such as pathology report 100, is difficult to access and analyze the data is either in paper form or in the form of scanned images. Because of the physical form of the data, as well as the fact that the data are unstructured, clinicians and clinical staff typically need to spend a lot of time to read through the pathology reports to obtain important clinical data, which is laborious, slow, costly, and error-prone.

Moreover, as the clinical data in the reports may include non-standardized terminologies, potential ambiguity and confusion may arise when clinicians interpret the non-standardized terminologies in the report, which can introduce error to the extraction of clinical data from the pathology reports.

A. System Architecture

Figure 3:
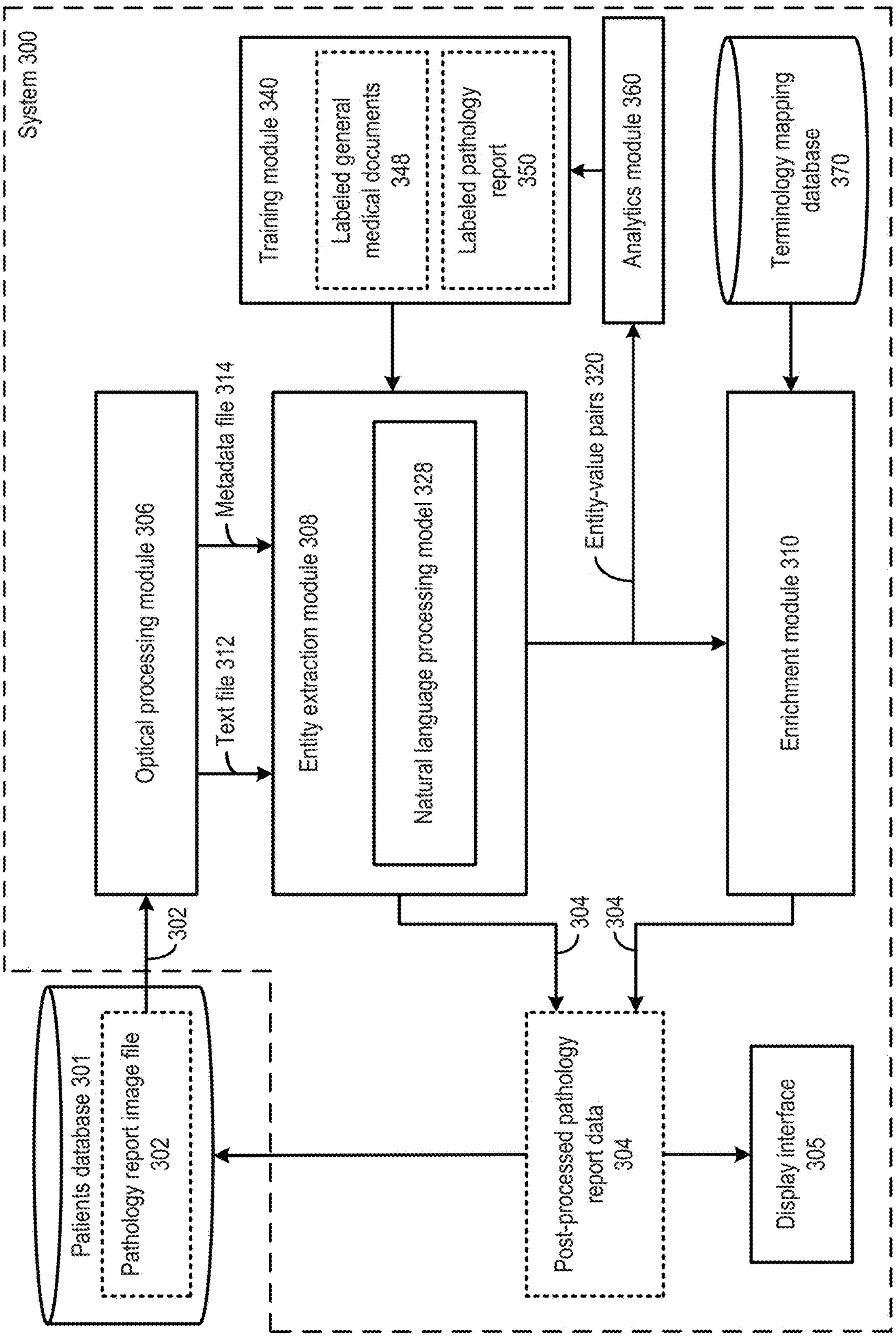
FIG. 3 illustrates an example of a system to perform automated extraction of information and enrichment of a pathology report.

FIG. 3 illustrates a system 300 that can perform automated extraction and enrichment of information of a pathology report to address at least some of the issues described above. System 300 can be part of a clinical portal application that implements an end-to-end enrichment workflow operation. Referring to FIG. 3, system 300 can receive, from a patients database 301, a pathology report image file 302 (e.g., of pathology report 100) as an input. System 300 can generate, as an output, post-processed pathology report data 304 (e.g., of pathology report 200). As to be described below, post-processed pathology report data 304 can include information extracted from pathology report image file 302, including pathology entities, such as those described in FIG. 2A and Table 1 above, and the associated values identified from pathology report image file 302. In addition, post-processed pathology report data 304 may also include enrichment information, such as standardized pathology entity values (e.g., a SNOMED concept). Post-processed pathology report data 304 can be written back to patients database 301 (or other clinical database) as structured medical data of a patient. In some examples, system 300 also includes a display interface 305 to display post-processed pathology report data 304 in a structured form (e.g., in the form of tables, populated forms). In some examples display interface 305 can also display pathology report image file 302 overlaid with text and graphical information based on post-processed pathology report data 304.

System 300 may include an optical processing module 306, an entity extraction module 308, and an enrichment module 310 to perform the information extraction and enrichment. Each module can include software instructions that can be executed on a computer system (e.g., a server, or in a cloud computing environment comprising multiple servers). In some examples, system 300 can be part of a clinical software platform (not shown in FIG. 3). Each module of system 300 can include an application programming interface (API) to communicate with the software platform to access different databases, such as patients database 301.

Referring to FIG. 3, optical processing module 306 can receive image file 302. The image file 302 can be received from various primary sources (at one or more healthcare institutions) including, for example, an EMR (electronic medical record) database, a PACS (picture archiving and communication system), a Digital Pathology (DP) system, an LIS (laboratory information system) including genomic data, an RIS (radiology information system), patient reported outcomes database, wearable and/or digital technologies, and social media. The image files can be in various formats such as, for example, Portable Document Format (pdf), or bitmap image file (BMP file). In some examples, the image files can be obtained by scanning the paper-form pathology reports.

After receiving image file 302, optical processing module 306 can perform an image recognition operation to identify text images from image file 302, generate text data from the text images, and generate an intermediate text file 312 including the text data. The image recognition operation may include, for example, optical character recognition (OCR) or optical word recognition. In both operations, optical processing module 306 can extract pixel patterns of characters (e.g., by identifying patterns of pixels with a dark color), compare each pixel pattern with pre-defined pixel patterns of characters, and determine which character (or which word/phrase) each pixel pattern represents based on the comparison. Optical processing module 306 can then store the character/word/phrase into text file 312. Optical processing module 306 can scan through image file 312 following a pre-determined pattern (e.g., raster scanning) to extract and process pixel patterns in a row from left to right and repeat the scanning for each row. Based on the scanning pattern, optical processing module 306 can generate a sequence of text strings (e.g., characters, words, phrases) and store the sequence of text strings in text file 312. In some examples, a metadata file 314, which indicates the pixel locations of each sequence of text strings, can also be generated by optical processing module 306. Metadata file 314 can be used by other applications as to be described below. Examples of metadata file 314 are shown in FIG. 4D.

Entity extraction module 308 can process text file 312, recognize entities (e.g., those listed in Table 1) from text file 312, and extract values associated with the entities. Entity extraction module 308 can generate entity-value pairs 320, with each pair including an extracted entity and a corresponding value. Entity extraction module 308 may include a natural language processing (NLP) model 328 to perform the recognition of entities and extraction of values. NLP model 328 can process a sequence of text from text file 312 and, based on recognizing a specific sequence of text strings, determine that a subset of text of the sequence is a value of a particular entity, and determine an entity-value pair for the subset.

B. Natural Language Processor Model

Figure 4A:
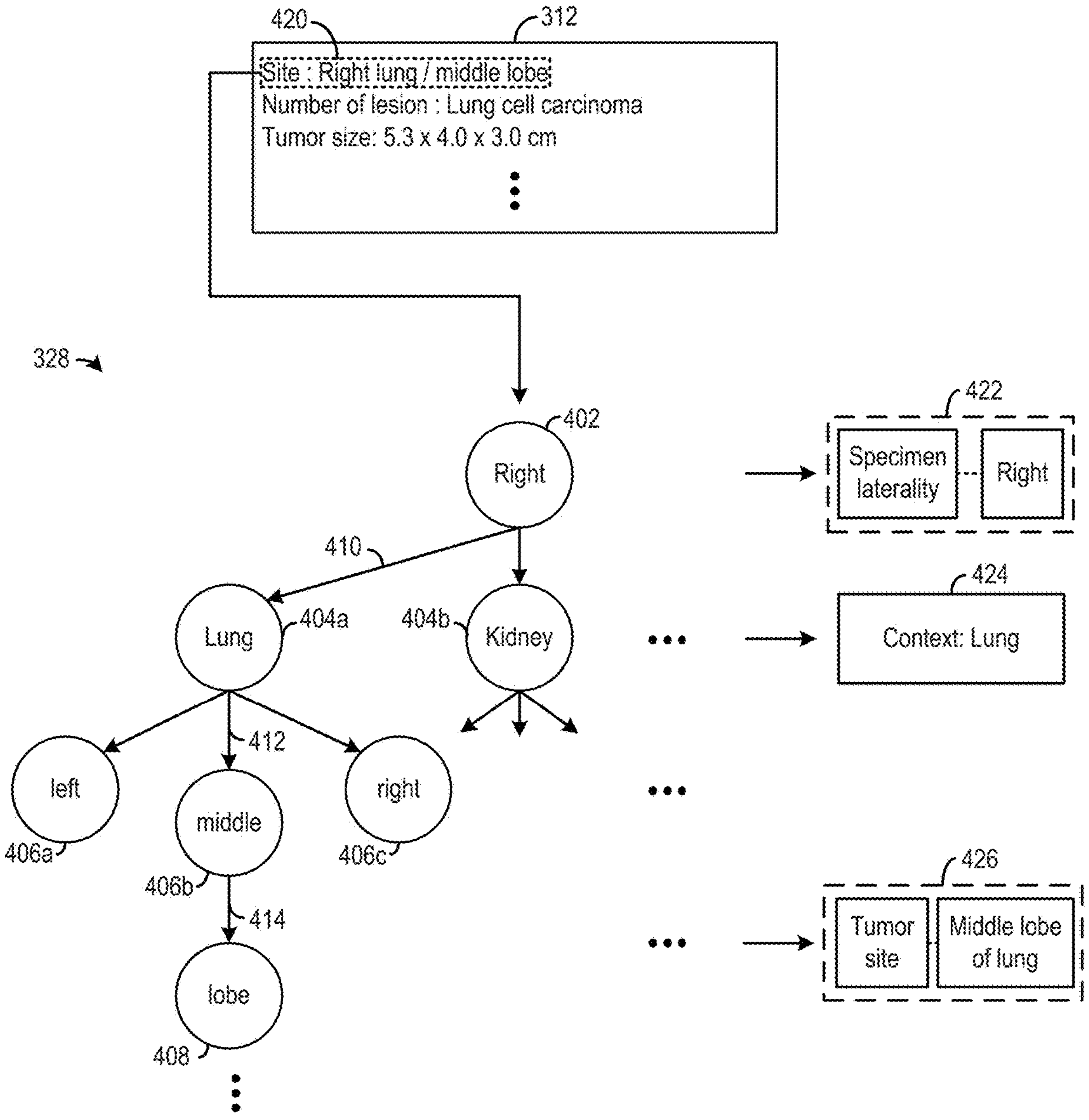
FIG. 4A, FIG. 4B, FIG. 4C, FIG. 4D, and FIG. 4E illustrate example internal components of system of FIG. 3 and their operations.

FIG. 4A illustrates an example of NLP model 328. As shown in FIG. 4A, NLP model 328 includes a graph comprising nodes, such as nodes 402, 404*a*, 404*b*, 406*a*, 406*b*, 406*c*, and 408. Each node can correspond to a text string. The nodes are connected by arcs in the graph, with the direction of arcs defining a sequence of text strings to be detected by NLP model 328. For example, nodes 402 and 404*a* are connected by an arc 410, nodes 404*a* and 406*b* are connect by an arc 412, whereas nodes 406*b* and 408 are connected by an arc 414. These nodes and arcs can define a sequence of text "right lung middle lobe." The nodes are also organized into hierarchies, and a detection output, which can be an entity-value pair, a context, etc., can be generated from each hierarchy. In the example of FIG. 4A, node 402 can be in a first hierarchy to detect the entity "specimen laterality", nodes 404*a* and 404*b* can be in a second hierarchy to detect the context, nodes 406*a*-406*c* and 408 can be in a third hierarchy to detect the entity "tumor site." The detection can be based on, for example, a parameterized equation that computes a score based on a degree of similarity between the input sequence of text strings and the text strings represented by the nodes, and a pre-determined entity-pair and/or context information can be output based on the score.

NLP model 328 can process a sequence of text strings, such as sequence 420, from text file 312. NLP model 328 can look for a sequence of nodes from the graph that matches (either exactly or to a threshold degree of closeness) to sequence 420, while skipping text strings (e.g., words, punctuations, symbols) that are not found in the graph. In some examples, the text strings of the nodes can be represented by vectors, and the threshold degree of closeness can be defined by a threshold of an aggregate Euclidean distance between the text strings in a sequence of nodes and in sequence 420. In some examples, the degree of closeness can also be defined by a threshold number of matching words between the sequence of nodes and sequence 420. In the example of FIG. 4A, NLP model 328 can process sequence 420 "site: right lung/middle lobe" by looking for a sequence of nodes from the graph that are closest to sequence 420, and may identify the sequence of nodes 402, 404*a*, 406*b*, and 408 to be closest to sequence 420 while ignoring the word "site" and punctuations ":" and "/". From the identified sequence, NLP model 328 may output an entity-value pair 422 (specimen laterality, right) from node 402 and a context 424 (lung) from node 404*a*. Moreover, based on context 424 indicating that the entity is related to a lung, NLP model 328 may further output an entity-value pair 426 (tumor site, middle lobe of lung) from nodes 406*b* and 408 from sequence 420. In some examples, NLP model 328 may output entity-value pair 426 even if the text string "lobe" is missing in sequence 420, based on detecting the sequence of text strings "right", "lung" and "middle" and that such a sequence leads to entity-value pair 426. The extracted entities and their values can be assembled into structured medical data and can be stored back to patients database 301.

In some examples, NLP model 328 can include a hierarchy of sub-models, such as a baseline NLP sub-model, as well as a pathology NLP sub-model specific for pathology entities. The baseline NLP sub-model can be used to provide a primary context for identifying sequences of text strings that include common medical terminologies that may (or may not) include pathology entities. The primary context can guide the identification of a text strings sequence that contains pathology entities.

Figure 4B:
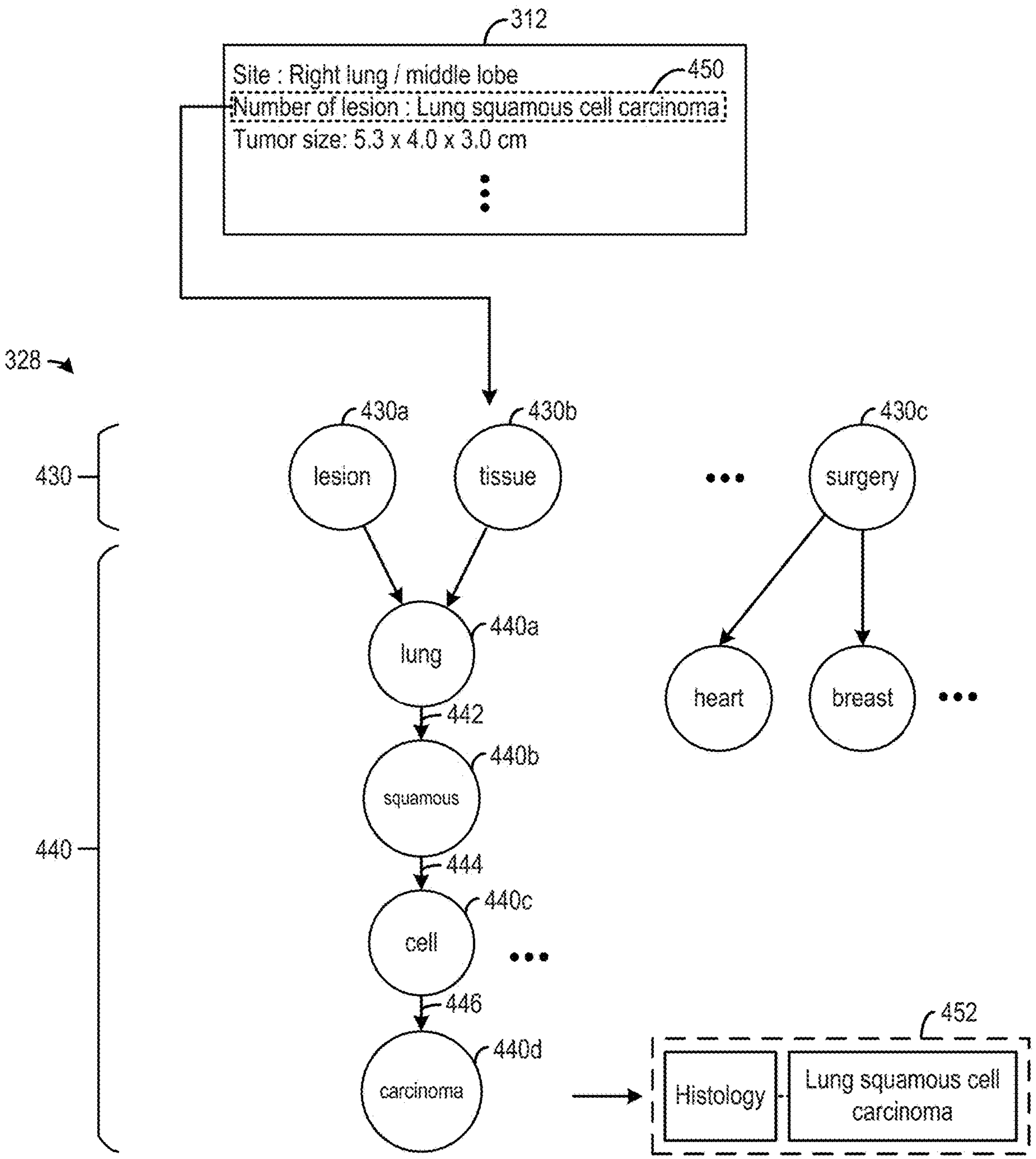

FIG. 4B illustrates another example of NLP model 328. As shown in FIG. 4B, NLP model 328 can include a baseline NLP sub-model 430 and a pathology NLP sub-model 440. Baseline NLP sub-model 430 can include, for example, nodes 430*a*, 430*b*, and 430*c*. Nodes 430*a* and 430*b* can be associated with generic medical terms that are related to histology, such as lesion, tissue, etc., whereas node 430*c* is associated with generic medical terms not related to histology, such as surgery. In addition, pathology NLP sub-model 440 can include nodes 440*a*, 440*b*, 440*c*, 440*d*, 440*e*, and 440*f*. Nodes 440*a*, 440*b*, 440*c*, and 440*d* can be linked by edges 442, 444, and 446 to form a sequence "lung squamous cell carcinoma." On the other hand, nodes 440*e* and 440*f* are associated with different organs to receive the surgery, such as heart and breast.

Baseline NLP sub-model 430 can provide a context/guidance for selecting which portion of pathology NLP sub-model 440 to process the sequence of text strings, such as sequence 450 shown in FIG. 4B. Specifically, from the text strings "number of lesions" in text strings sequence 450, baseline NLP sub-model 430 can select nodes 440*a*-440*d* of pathology sub-model 440 to process the rest of text strings sequence 450. Pathology sub-model 440 can then compare the sequence associated with nodes 440*a*-440*d* ("lung squamous cell carcinoma") with the rest of text strings sequence 450. Based on finding that the sequences match, NLP sub-model 430 may output an entity-value pair 452 (histology, lung squamous cell carcinoma).

Notice that the NLP model topology in FIG. 4A and FIG. 4B are provided as illustrative examples. It is understood that NLP model 328 can take on other forms, such as CRF (Conditional Random Field) Classifier as Linear Chain-sequence model, CNN Bi-LSTM (Convolutional Neural Network-Bi-directional Long-Term Short Term Memory), etc.

C. Enrichment Operation

Referring back to FIG. 3, enrichment module 310 can perform an enrichment operation to improve the quality of the medical information extracted from pathology report image file 302. One example enrichment operation may include converting entity values in the pathology report to standardized values, such as SNOMED concepts, as shown in FIG. 2B. System 300 may further include a terminology mapping database 370 to support the enrichment operations by enrichment module 310.

Figure 4C:
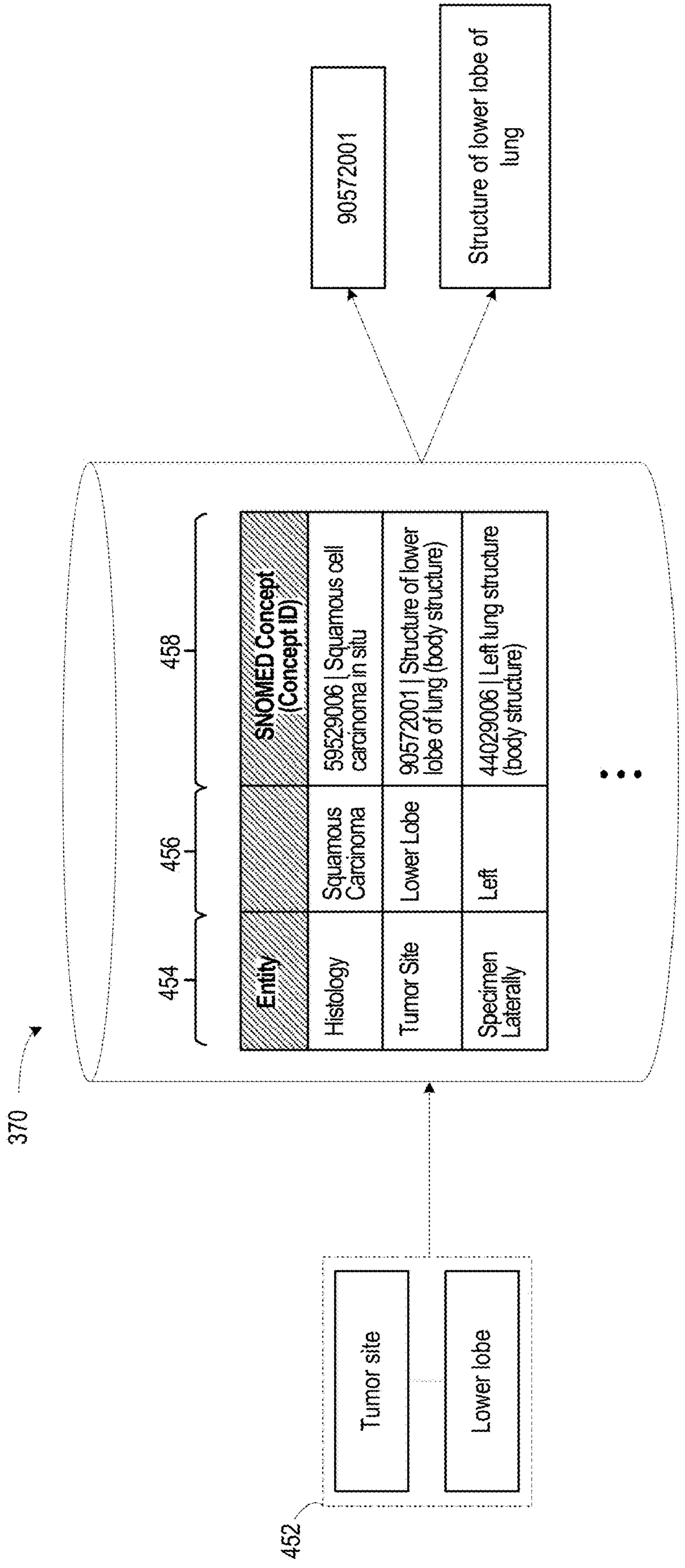
Figure 4D:
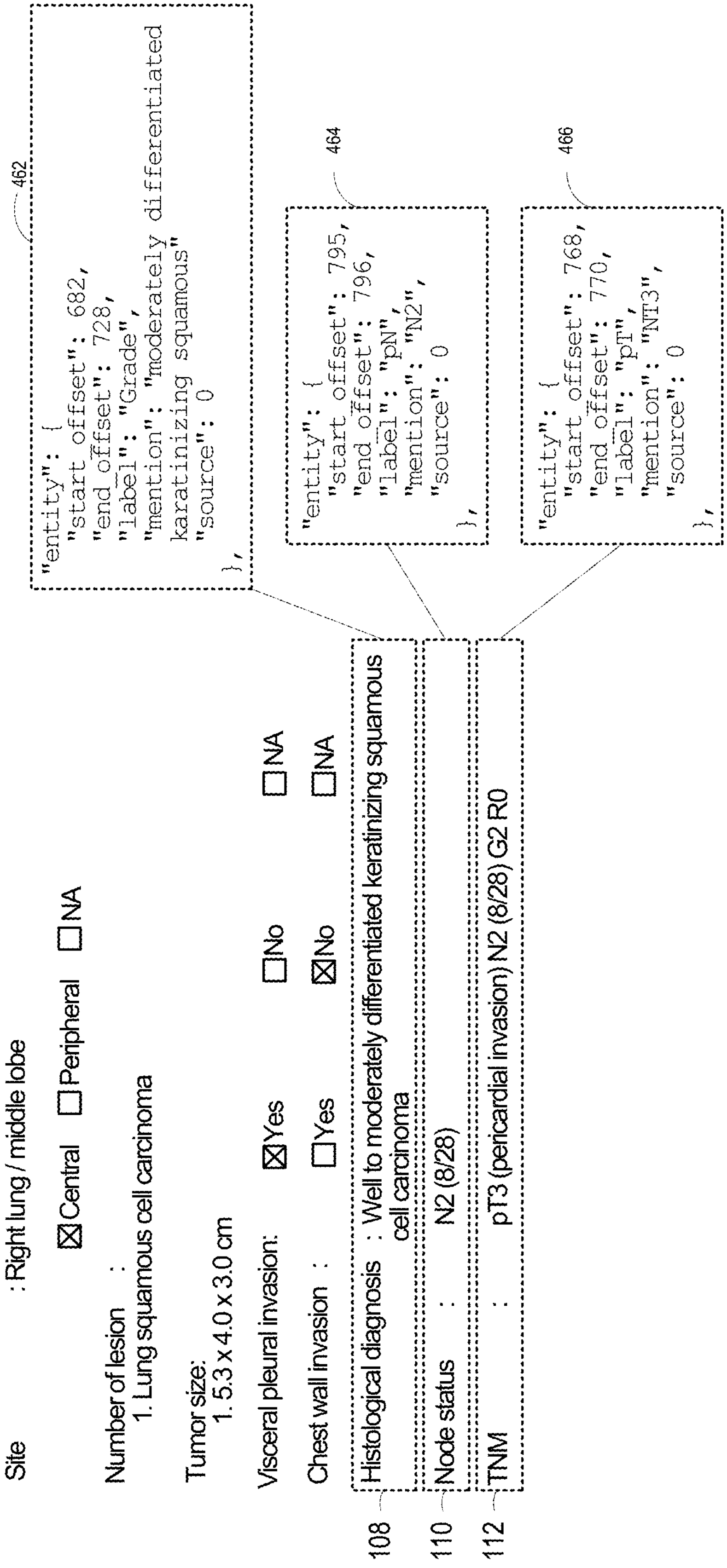

FIG. 4C illustrates an example enrichment operation performed by enrichment module 310 using terminology mapping database 370 which can include a mapping between an entity-value pair to a standard terminology, such as a SNOMED concept and a concept ID. In FIG. 4C, the mapping can be in the form of a mapping table comprising an entity column 454, a value column 456, and a SNOMED concept column 458. For each entity-value pair, enrichment module 310 can perform a search for the entity and the value in, respectively, entity column 454 and value column 456, and the associated SNOMED concept and concept ID in SNOMED concept column 458. In the example of FIG. 4C, for an entity-value pair 452 of "tumor site, lower lobe", enrichment module 310 can identify "tumor site" in entity column 454, "lower lobe" in value column 456, and the SNOMED concept of "structure of lower lobe of lung" and a concept ID of 90572001 from SNOMED concept column 458 370.

In some examples, as part of the enrichment process, enrichment module 310 can replace each entity-value pair extracted by entity extraction module 308 that has a mapping to a SNOMED concept with an entity-SNOMED concept pair, and store the entity-SNOMED concept pair in post-processed pathology report data 304. The replacement of an entity-value pair with its SNOMED concept can enrich post-processed pathology report data 304 by including standard terminologies in the report, which can reduce the risk of misinterpretation and ambiguity associated with non-standard values of entities for a human reader. In some examples, the entity-value pairs can also be replaced with SNOMED concept IDs to reduce data size of post-processed pathology report data 304. Such arrangements can also facilitate processing of post-processed pathology report data 304 by an application. Specifically, since an entity-value pair may have multiple alternative versions of values representing the same concept, an application that extracts and interprets an entity-value pair needs to have built-in capabilities to recognize the multiple alternative versions of the values to recognize the associated concept. On the other hand, an application can parse a SNOMED concept ID and link a concept with the concept ID unambiguously, which can reduce the complexity of the application.

D. Display Interface to Support Enrichment Operation

Referring back to FIG. 3, system 300 may include a display interface 305 to display post-processed pathology report data 304. In some examples, display interface 305 can display the structured medical data of post-processed pathology report data 304 in a structured form (e.g., in the form of tables, populated forms) to enable a user of the portal (e.g., clinician, clinician staff) to efficiently identify the medical information they look for. In some examples, display interface 305 can display pathology report image file 302, as well as highlight markups (text) overlaid on the text strings, which NLP 328 determines to represent pathology entities. The highlight markups are selectable. Display interface 305 can also detect a selection of the highlight marking over a set of text strings, and display a pop-up window including the entity label and value, as well as other enrichment information (e.g., standardized data based on SNOMED) of the selected text strings.

The operation of display interface 305 can be based on metadata file 314, which indicates that the pixel locations of each sequence of text strings can also be generated by optical processing module 306. FIG. 4D illustrates examples of metadata file 314. As shown in FIG. 4D, from pathology report 100, metadata 462, 464, and 466 can be generated based on entity-value pairs extracted from, respectively, sections 108, 110, and 112. Each metadata set can indicate the start and end pixel locations ("start_offset" and "end_offset") of the text strings from which an entity-value pair is extracted, the label of the entity, and the value of the entity ("mention"). In some examples, the start and end pixel locations can be presented by a pixel number starting from top left of the image and counting in a rasterized fashion. In some examples, the start and end pixel locations can also be represented by two-dimensional pixel coordinates in the image.

Figure 4E:
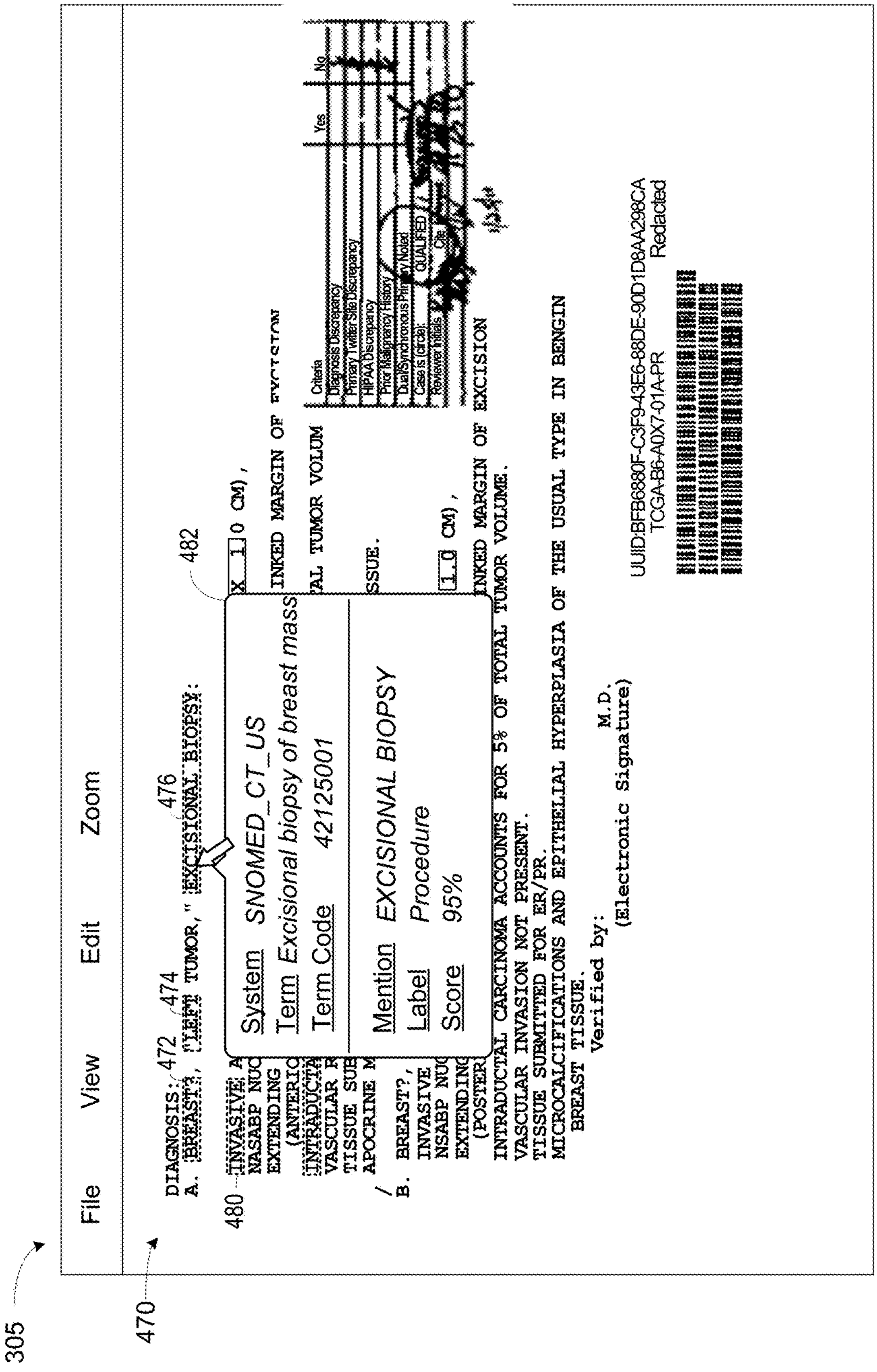

FIG. 4E illustrates an example of display interface 305. As shown in FIG. 4E, display interface 305 can display an image 470 of a pathology report, as well as highlight markups such as highlight markups 472, 474, 476, and 480. Each highlight marking is overlaid on image 470 at start and pixel locations indicated in the metadata of the text strings from which an entity-pair is extracted. In addition, each highlight marking is selectable (e.g., by moving mouse cursor over the highlight marking) to show the underlying metadata. For example, in FIG. 4E, display interface 305 can detect that a mouse cursor is moved over highlight marker 476 for the text strings "excisional biopsy". Based on the pixel location of the mouse cursor, display interface 305 can identify, from all the metadata generated for image 470, the metadata having a range of pixel locations (represented by start_offset and end_offset) that covers the mouse cursor's pixel location. Display interface 305 can then extract, from the identified metadata, the SNOMED information, the text strings, the label of the entity, as well as a confidence level (score) of the extraction, and display the extracted information in a pop-up window 482.

E. Training of Natural Language Processor

Referring back to FIG. 3, NLP model 328 can be a machine-learning model that is trained. As shown in FIG. 3, system 300 may include a training module 340, which can train NLP model 328. Training module 340 can train NLP model 328 based on labeled general medical documents 348 and labeled pathology report 350. General medical documents 348 can include various categories of biomedical literatures, reports, etc. The training create nodes representing words of medical terminologies, as well as edges representing the sequential relationships among the words, such as those of NLP model 328 of FIG. 4A. As part of the training operation, a sequence of text strings with a particular label (e.g., a labeled entity, a labeled entity value, a labeled context) can be input to NLP model 328 to determine whether NLP outputs correct entity-value pairs and/or context information. If training module 340 determines that NLP model 328 does not output correct entity-value pairs and/or context information (e.g., based on comparing the labelled entity/entity value of the sequence of text strings and the entity-value pairs output by the NLP model for the sequence of text strings), the training module 340 can modify NLP model 328 by creating new nodes representing new words, adding edges between existing nodes, etc. The decision mechanism to output an entity-value pair (e.g., a parameterized equation) can be also be updated (e.g., by updating the parameters) to increase the likelihood of outputting the correct entity-pair and/or context information.

Figure 5A:
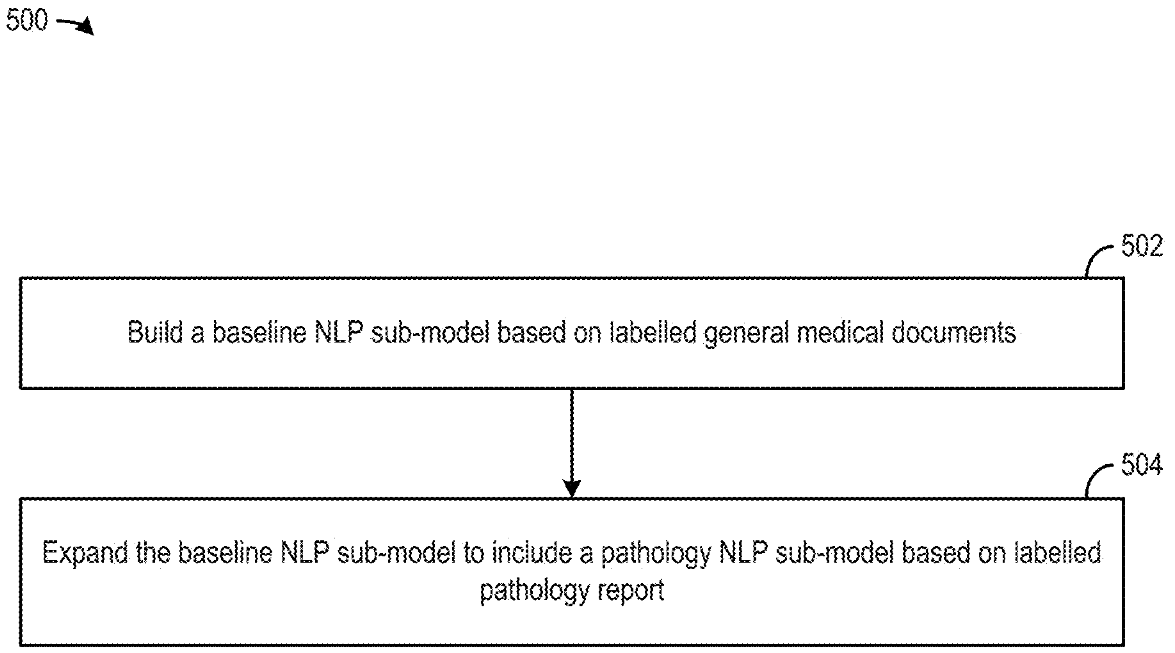

FIG. 5A, FIG. 5B, FIG. 5C, FIG. 5D, and FIG. 5E illustrate examples of a training operation of NLP model 328. As shown in FIG. 5A, a training operation 500 of NLP model 328 can be performed in a two-step process. In step 502, a baseline NLP sub-model, such as baseline NLP sub-model 430, can be built based on labeled general medical documents. As described above, baseline NLP sub-model 430 can be used to provide a primary context for identifying sequences of text strings that include common medical terminologies, which may (or may not) include pathology report terminologies. Baseline NLP sub-model 430 can be trained based on training data derived from biomedical articles from various major sources such as, for example, PubMed Central®, a free full-text archive of biomedical and life sciences journal literature at the U.S. National Institutes of Health's National Library of Medicine. The training data can include sequence of text strings with a particular label (e.g., a labeled entity, a labeled entity value, a labeled context) extracted from the biomedical articles.

In step 504, the baseline NLP sub-model can be trained using labeled sequences of text strings from pathology reports, thereby expanding the baseline NLP sub-model to include a pathology NLP sub-model (e.g., pathology NLP sub-model 440) that can detect sequences of pathology terminologies. Step 504 can be performed using CoNLL (Conference on Natural Language Learning) files. A CoNLL file may include texts extracted from other pathology reports, where each text can be tagged with either an entity label or an indication of being a non-entity. The NLP can be trained based on the CoNLL files from multiple pathology reports. In some examples, the training can be specific for a hospital, a clinical group, an individual clinician, etc., such that an NLP can be trained to learn the preference of words of the hospital/clinical group/clinician, which can maximize the accuracy of extraction of entities and their values.

Figure 5B:
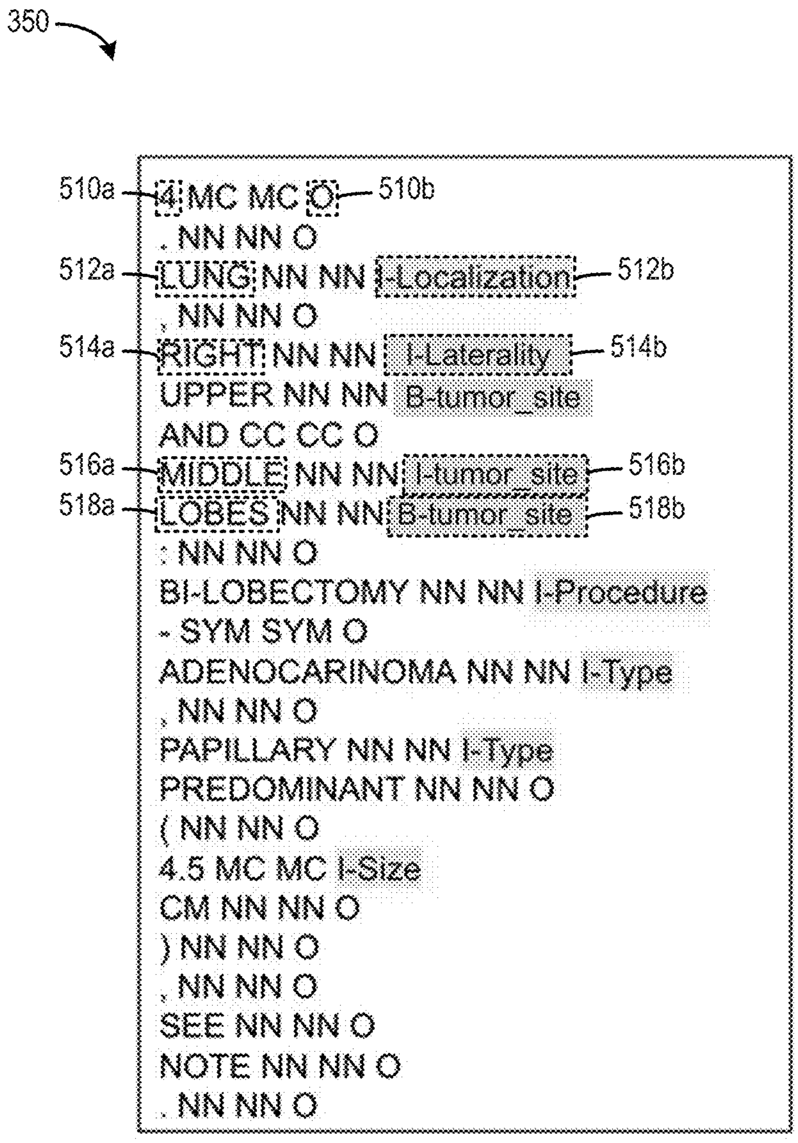

FIG. 5B illustrates an example of a labeled pathology report 350, which can be in a CoNLL format. Labeled pathology report 350 includes text strings to be input into NLP model 328, as well as labels that indicate the entities of the text strings, which can be used by training module 340 to guide the output of NLP model 328 to perform the training. A label can represent a reference entity to be output by NLP model 328 for a sequence of text strings. Training module 340 can then update the parameters of NLP model 328 based on differences between the reference entity and the entity actually output by NLP model 328 for the sequence of text strings. Labeled pathology report 350 can be generated by human beings (e.g., clinicians, clinician staff) who can identify the information contained in the pathology report and associate the information with the label. The identification of information and association with a label can be based on a universal standard (e.g., SNOMED) and can also be specific to the habit/practice of a particular clinician, a medical group, a health care provider, etc. For example, a clinician may have a specific way of reporting tumor site location, and the pathology report from the clinician can be labeled to indicate such to train NLP model 328.

As shown in FIG. 5B, each line of labeled pathology report 350 may include a text character/string/phrase, such as text strings 510*a*, 512*a*, 514*a*, 516*a*, 518*a*, etc. Each text string is linked with a label, which can indicate a context, an entity, a skipped word, and their positions in a sequence. For example, label 512*b* for the word "lung" is "I-localization", which indicates that the word "lung" belongs to the context "localization," while "I" refers to the word "lung" being found in the beginning of a sequence for which the context "localization" is to be identified. As another example, label 514*b* is "I-laterality", which indicates that the word "right" belongs to the entity "laterality," while "I" refers to the word "right" being found in the beginning of a sequence for which the entity "laterality" is to be identified. Further, labels 516*b* and 518*b* are, respectively, "I-tumor_site" and "B-tumor_site." The labels can indicate that the words "middle" and "lobes" belong to the entity "tumor_site," with the word "middle" to be found in the beginning of a sequence for the entity, whereas "B" indicates that the word "lobes" is to be found in the middle of the sequence for the entity. Further, label 510*b* indicates that the word "4" is a skipped text which will not be processed by NLP model 328.

Figure 5C:
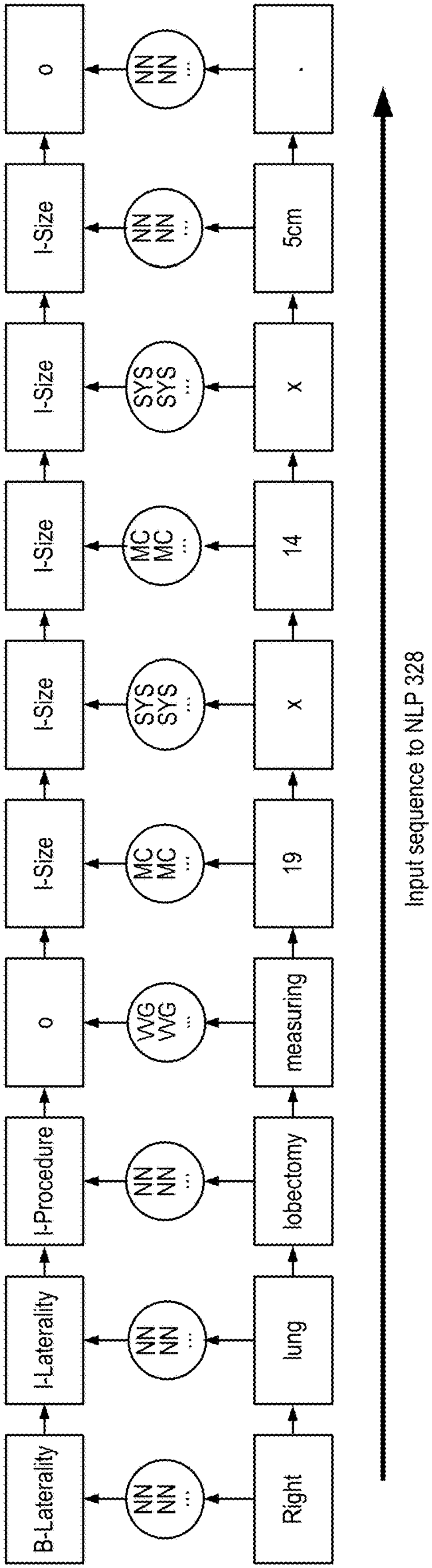

FIG. 5C shows how a sequence of labeled text strings can be processed by NLP model 328. For each text in the sequence, training module 340 can determine whether the text is in a node of NLP model 328, and can add a node and/or an edge to the model if the text string is not found. Moreover, training module 340 can compare the label (e.g., entity "laterality") with the output of NLP model 328, and update the decision mechanism if the output do not match.

Figure 5D:
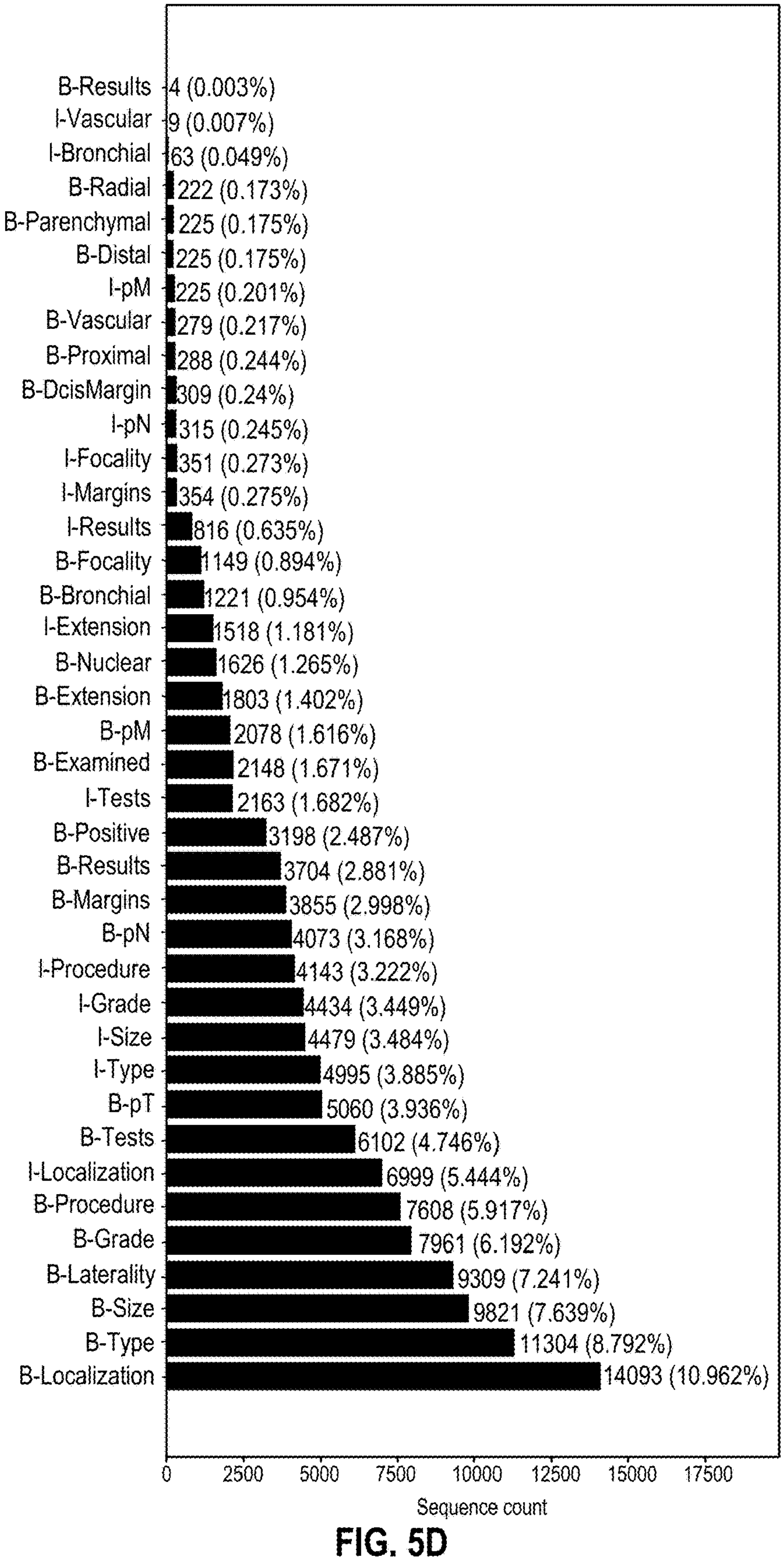

FIG. 5D illustrates an example distribution 520 of different entities in the labeled sequence of text strings used to train NLP 328, whereas FIG. 5E illustrates various metrics in measuring the accuracy of entity extraction by NLP 328. As shown in FIG. 5D, a relatively large portion of the text strings sequence is labeled "B-grade," "B-laterality," "B-size," "B-type," and "B-localization" (6%-11%), as these text strings are more commonly found in the middle of a sequence. Moreover, a relatively small portion of the text strings sequence is labeled "B-results," "I-vascular," "I-bronchial," and "I-margins" (0.003%-0.275%) as these text strings are more rare. Distribution 520 can be based on a corpus of documents from PubMed Central® and can include about 2 million words.

FIG. 5E illustrates a table 530 of extraction accuracy metrics for the entities output by NLP model 328 after the model is trained a corpus of documents from PubMed Central® having distribution 520 of entities. The extraction accuracy metrics includes a true positive (tp) count, a false positive (fp) count, a false negative (fn) count, a precision (prec), a recall (rec), and an F1 score (f1) for each entity. The true positive count counts the number of text strings sequences that NLP 328 correctly detects as including a particular entity. The false positive count counts the number of text strings sequences that do not include a particular entity but NLP 328 incorrectly detects as including that entity. The false negative count counts the number of text strings sequences that include a particular entity but NLP 328 incorrectly detects as not including that entity. Precision, also known as positive predictive value, refers to the fraction of correct positive detections (flagging as a sequence including an entity) out of all positive detections (correct and incorrect detections). Recall, also known as sensitivity, refers to the fraction of correct positive detections out of all detection results (true positive and false negative detections). Precision and recall can be computed based on the following equations:

$$\text{Precision} = \frac{tp}{tp + fp} \quad \text{(Equation 1)}$$

$$\text{Recall} = \frac{tp}{tp + fn} \quad \text{(Equation 2)}$$

The F1 scores are calculated to provide a confidence level of a detection. A good F1 score is an overall reflection of both a good precision and a good recall. As the NLP model is used in healthcare domain, a higher precision is more favored than a higher recall.

$$F1 = \frac{\text{precision} \times \text{recall}}{\text{precision} + \text{recall}} \quad \text{(Equation 3)}$$

As shown in FIG. 5E, the average F1 score is about 0.85, with the F1 scores of a majority of the entities are above 0.9. The entities having a lower F1 score, such as I-margins (0.4), are generally the ones that are not well represented in FIG. 5D, which makes it difficult for the NLP model to detect those entities accurately.

The training of NLP model 328 can be performed off-line, or performed while processing the pathology report image files to dynamically update NLP model 328. For example, the training of NLP model 328 can be performed as part of a maintenance operation before NLP model 328 is used to process the pathology report image files. As another example, system 300 may include an analytics module 360, which can analyze the correctness of the outputs (e.g., entity-value pair, context) of NLP model 328 from processing the pathology report image files, and if the outputs are incorrect (or if a number of incorrect outputs exceeds a threshold), analytics module 360 can trigger training module 340 to retrain NLP model 328. As part of the retraining, the text sequence in the pathology report image file from which incorrect outputs are generated, with correct labels attached, can be added to labeled pathology reports 350 to retrain NLP model 328.

III. TUNING OF IMAGE RECOGNITION OPERATION

In addition, various techniques can determine various parameters of the image recognition operation to improve the extraction accuracy of the NLP. The parameters for optical character recognition (OCR) operation may include an erosion value, a page iterator level, a page segmentation mode, or a scaling factor. The erosion value can indicate whether a blurred lines smoothing operation is performed. The page iterator level can refer to a granularity of the image recognition operation—whether it is performed by treating the entire page as a block or treating sections within a page (a paragraph, a line, a word, a character, etc.) as blocks to increase the granularity of the image recognition operation. The page segmentation mode can detect an slanted orientation of the page being processed and adjust the image recognition operation to correct for the slanted orientation. The scaling factor can set a zoom level to zoom into or zoom out of the image to be processed.

In some examples, the tuning of these OCR parameters can be based on the outputs of NLP 328. Specifically, the image recognition operation can be pre-configured based on a first set of parameters values. The pre-configured OCR operation can be performed on images of pathology reports to extract text strings, and the text strings can be input to the NLP to extract pathology entities. The OCR parameters can then be adjusted based on the accuracy of extraction by the NLP.

Figure 6:
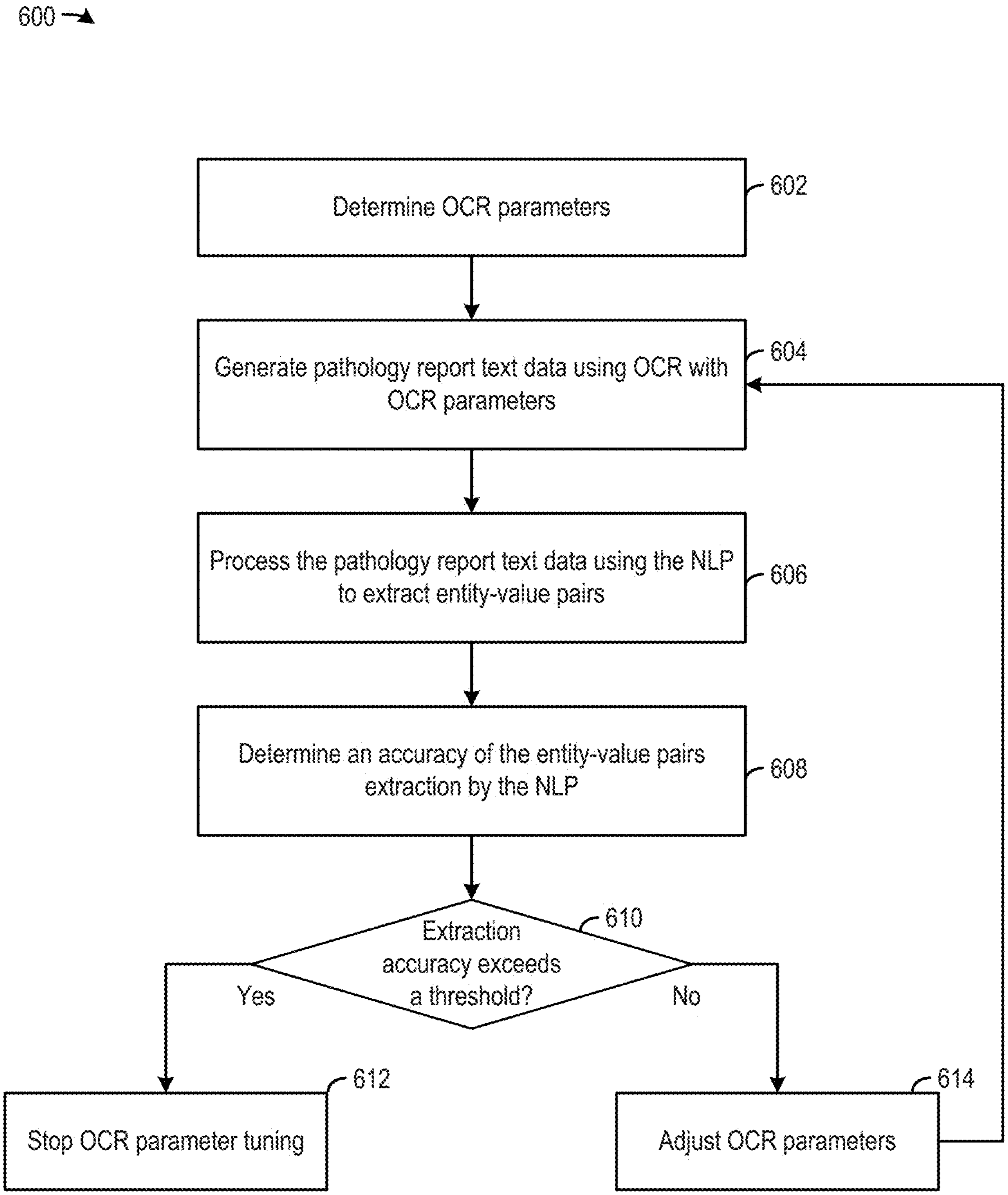
FIG. 6 illustrates an example operation to determine the parameters of an image recognition operation in the system of FIG. 3.

FIG. 6 illustrates an example of a tuning operation 600 to tune the OCR parameters based on the outputs of NLP 328.

In step 602, a set of OCR parameters, such as erosion value, page iterator level, page segmentation mode, scaling factor, etc., can be determined. Those parameters can be set at default values or values determined from a parameter sweeping operation. A parameter sweeping operation can be performed for the image recognition operation on the same set of images of pathology reports, in which the image recognition operation can be performed iteratively, with each iteration performed based on a different combination of values of the parameters. The text recognition accuracy for each iteration can then be measured, and a combination of parameters' values that lead to the highest text recognition accuracy can be used to configure the image recognition operation for the workflow.

In step 604, pathology report text data 312 can be generated by applying the OCR model with the OCR parameters on images of pathology reports.

In step 606, the pathology report text data can be processed using the NLP to extract entity-value pairs.

In step 608, an accuracy of the extraction of the entity-value pairs by the NLP is determined. The accuracy can be determined based on, for example, determining an F1 score based on Equations 1-3 above.

In step 610, it is determined whether the extraction accuracy exceeds a threshold. For example, it is determined whether the F1 score exceeds 0.75.

If the extraction accuracy exceeds the threshold, the OCR parameter tuning operation can be stored in step 612. But if the extraction accuracy is below the threshold, the OCR parameters are adjusted in step 614, and then step 604 is repeated. The parameters being adjusted can be selected based on identifying the entity-value pairs having the lowest precision. As an illustrative example, it may be determined that certain words in the pathology reports that belong to the entity-value pairs with low precision have very small image sizes. In such example, the scaling factor of the OCR operation can be increased.

Besides providing accuracy measurements for entity-value pair extraction to pinpoint a specific OCR parameter to be adjusted, tuning the OCR parameters based on the NLP output can be advantageous in other scenarios. For example, in a case where the image file contain notes by a particular physician which may include non-standard codes and phrases, if the OCR outputs are compared against standardized phrases to determine the text recognition accuracy, the comparison may lead to incorrect conclusion about the text recognition accuracy. For example, the text strings that contain non-standard codes and phrases may be incorrectly flagged as wrong when in fact the OCR operation extracts the text strings correctly. On the other hand, as the NLP model has been trained to recognize non-standard codes and phrases, as well as standardized terminologies, using the NLP output to determine the text recognition accuracy can ensure that the text recognition accuracy measurement is less affected by the presence of non-standard codes and phrases in the OCR output.

IV. EXAMPLE APPLICATIONS OF POST-PROCESSED PATHOLOGY REPORT DATA

Figure 7:
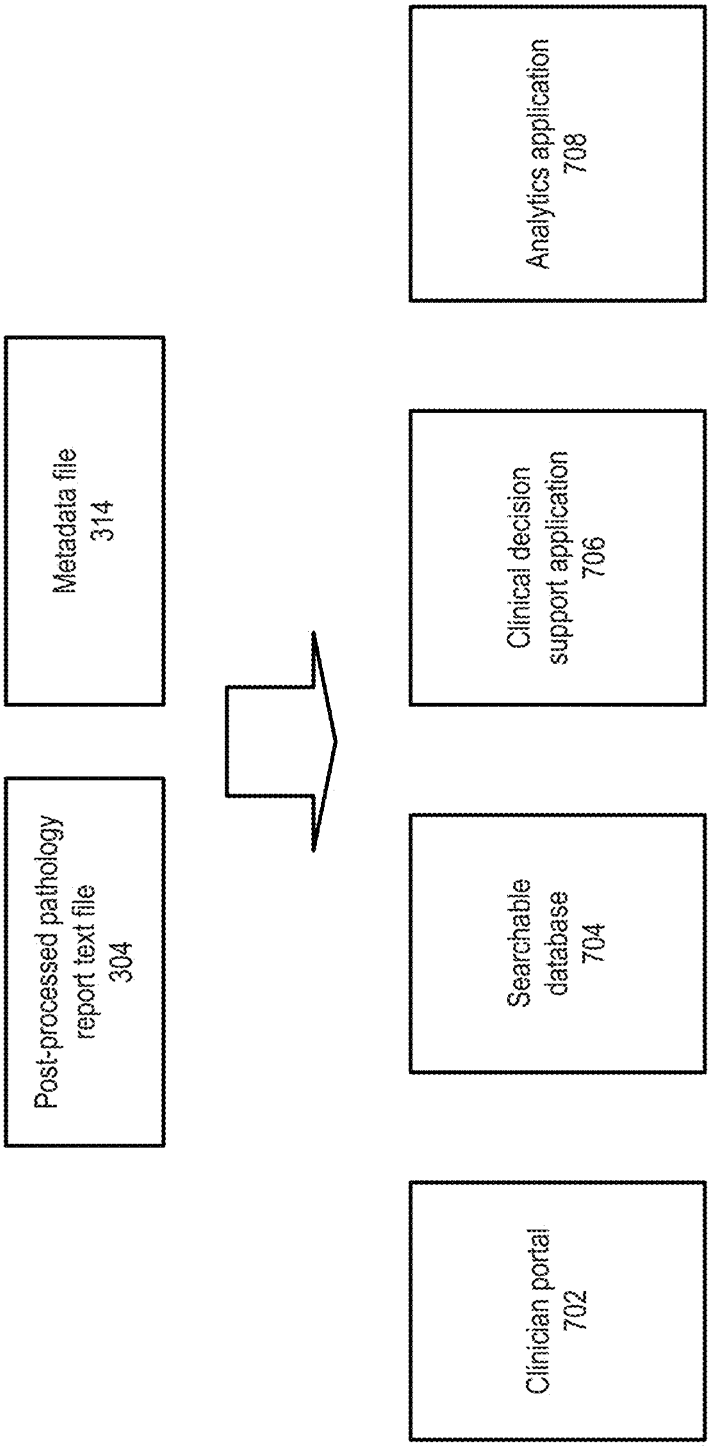
FIG. 7 illustrates example applications supported by the output of system of FIG. 3.

FIG. 7 illustrates example applications of post-processed pathology report data 304 and metadata file 314. As shown in FIG. 7, post-processed pathology report data 304 can be provided to a clinician portal 702, which can include display interface 305 of FIG. 4E. In some examples, clinician portal 702 can display the entity-value pairs (and/or SNOMED concepts) to a user in a pre-determined structured form (e.g., in the form of tables, populated forms) to enable a user of the portal (e.g., clinician, clinician staff) to efficiently identify the medical information they look for. As another example, clinician portal 702 can also display an image of the original pathology report, but with some or all of the text strings replaced with the entity-value pairs and/or SNOMED concepts, or with the text strings highlighted and tagged with the entity-value pairs/SNOMED concepts. Clinician portal 702 can perform the highlighting of the text strings in the image based on the pixel locations of the text strings indicated in metadata file 314, as described in FIG. 4E.

As another example, post-processed pathology report data 304 can be provided to a searchable database 704, from which the entities and their values (standardized or not) can be retrieved based on search queries. The searchable database, as well as the structured medical data, can also be made available to various applications, such as a clinical decision support application 706, an analytics application 708, etc., for processing. For example, the clinical decision support application can retrieve entities relevant to a clinical decision (e.g., diagnosis, procedure history, medication history) and their values from the database, and process the entities to generate an output to support a clinical decision. An analytics application can also obtain entities related to, for example, treatment history and diagnosis from the pathology reports of a large number of patients and perform analysis to obtain insights in healthcare delivery and quality of care.

V. METHOD

Figure 8:
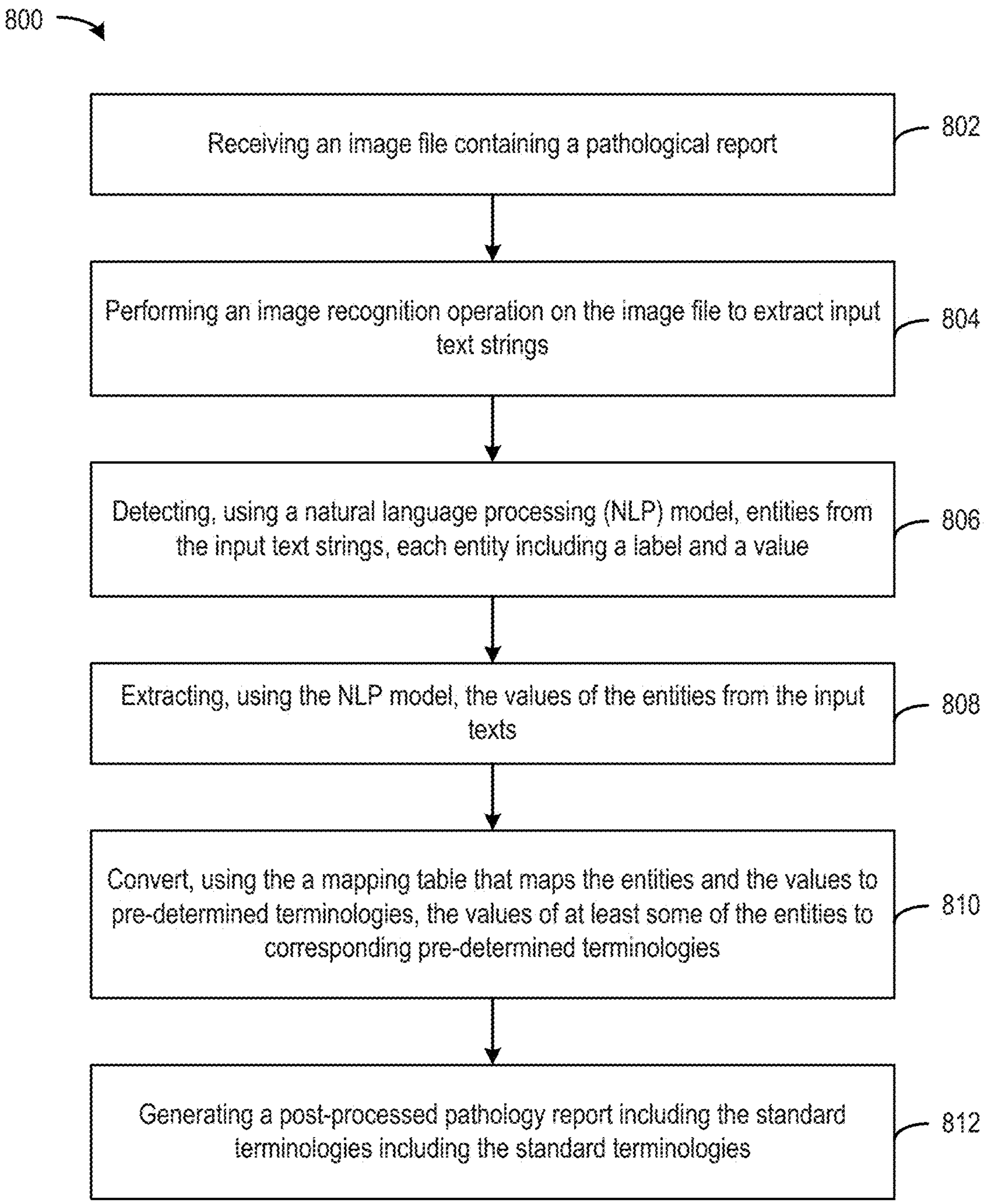
FIG. 8 illustrates a method of performing automated extraction of information and enrichment of a pathology report.

FIG. 8 illustrates a method 800 of automated extraction of information and enrichment. Method 800 can be performed by, for example, system 300 of FIG. 3.

At step 802, optical processing module 306 receives an image file (e.g., image file 302) containing a pathology report. The image file can be received from various primary sources (at one or more healthcare institutions) including, for example, an EMR (electronic medical record) database, a PACS (picture archiving and communication system), a Digital Pathology (DP) system, an LIS (laboratory information system) including genomic data, an RIS (radiology information system), patient reported outcomes database, wearable and/or digital technologies, and social media. The image files can be in various formats such as, for example, Portable Document Format (pdf), or bitmap image file (BMP file), and can be obtained by scanning the paper-form pathology reports.

In step 804, after receiving the image file, optical processing module 306 can perform an image recognition operation to extract input text strings from the image file. The extraction may include identifying text images from the image file, generating text data represented by the text images, and generating an intermediate text file (e.g., text file 312) including the text data. The image recognition operation may include, for example, optical character recognition (OCR) or optical word recognition. In both operations, optical processing module 306 can extract pixel patterns of characters (e.g., by identifying patterns of pixels with a dark color), compare each pixel pattern with predefined pixel patterns of characters, and determine which character (or which word/phrase) each pixel pattern represents based on the comparison. Optical processing module 306 can then store the character/word/phrase into text file 312. Optical processing module 306 can scan through image file 312 following a pre-determined pattern (e.g., raster scanning) to extract and process pixel patterns in a row from left to right, and repeat the scanning for each row. Based on the scanning pattern, optical processing module 306 can generate a sequence of text strings (e.g., characters, words, phrases) and store the sequence of text strings in text file 312.

In step 806, entity extraction module 308 can detect, using a natural language processing (NLP) model (e.g., NLP model 328), entities from the input text strings, with each entity including a label and a value.

In step 808, entity extraction module 308 can also extract, using the NLP model, the values of the entities from the input text strings. Specifically, NLP model 328 can process a sequence of text from text file 312 and, based on recognizing a specific sequence of text strings, determine that a subset of text of the sequence is a value of an entity, and determine an entity-value pair for the subset. As described above, NLP model 328 includes a graph comprising nodes. Each node may correspond to a text string and can be connected to another node via an arc. The nodes and arcs can define a sequence of text. The nodes are also organized into hierarchies, and a detection output, which can be an entity-value pair, a context, etc., can be generated from each hierarchy. The detection can be based on, for example, a parameterized equation that computes a score based on a degree of similarity between the input sequence of text strings and the text strings represented by the nodes, and a pre-determined entity-pair and/or context information can be output based on the score. NLP model 328 can process a sequence of text strings by searching for a sequence of nodes from the graph that matches (either exactly or to a pre-determined degree of closeness) to the sequence. From the identified sequence, NLP model 328 may output the entity-value pairs. In some examples, NLP model 328 may include a baseline NLP sub-model 430 and a pathology NLP sub-model 440, and NLP model 328 can be trained in a two-step process: first with text strings sequences from generic medical documents and then with text strings sequences from pathology reports, as described in FIG. 5A-FIG. 5D.

In some examples, the parameters of image recognition operation can also be adjusted based on the accuracy of outputs of NLP model 328. Specifically, as described in FIG. 6, the image recognition operation at optical processing module 306 can be pre-configured based on a first set of parameters values. The pre-configured image recognition operation can be performed on images of pathology reports to extract text strings, and the text strings can be input to the NLP to extract pathology entities. The parameters of the image recognition operation can then be adjusted based on the accuracy of extraction by the NLP.

In step 810, enrichment module 310 can convert, using a mapping table that maps the entities and the values to pre-determined terminologies, the values of at least some of the entities to corresponding pre-determined terminologies. The pre-determined terminologies can include standard terminologies defined based on a universal standard, such as SNOMED. The mapping table can be based on data stored in a terminology mapping database, which can include a mapping between an entity-value pair to a standard terminology, such as a SNOMED concept and a concept ID. For each entity-value pair and the associated context, enrichment module 310 can perform a search for the associated SNOMED concept and concept ID in terminology mapping database 370.

In step 812, enrichment module 310 can generate a post-processed pathology report including the entities detected from the input text strings and the corresponding pre-determined terminologies. Specifically, enrichment module 310 can replace each entity-value pair from NLP model 328 that has a mapping to a SNOMED concept with the SNOMED concept, and store the SNOMED concepts in the post-processed pathology report text file. In some examples, the entity-value pairs can also be replaced with SNOMED concept IDs to reduce data size of the post-processed pathology report text file. The post-processed pathology report can then be provided to support various applications, such as for displaying in a clinician portal, to be stored in a searchable database, to be processed by a clinical decision support application, an analytics application, etc.

VI. COMPUTER SYSTEM

Figure 9:
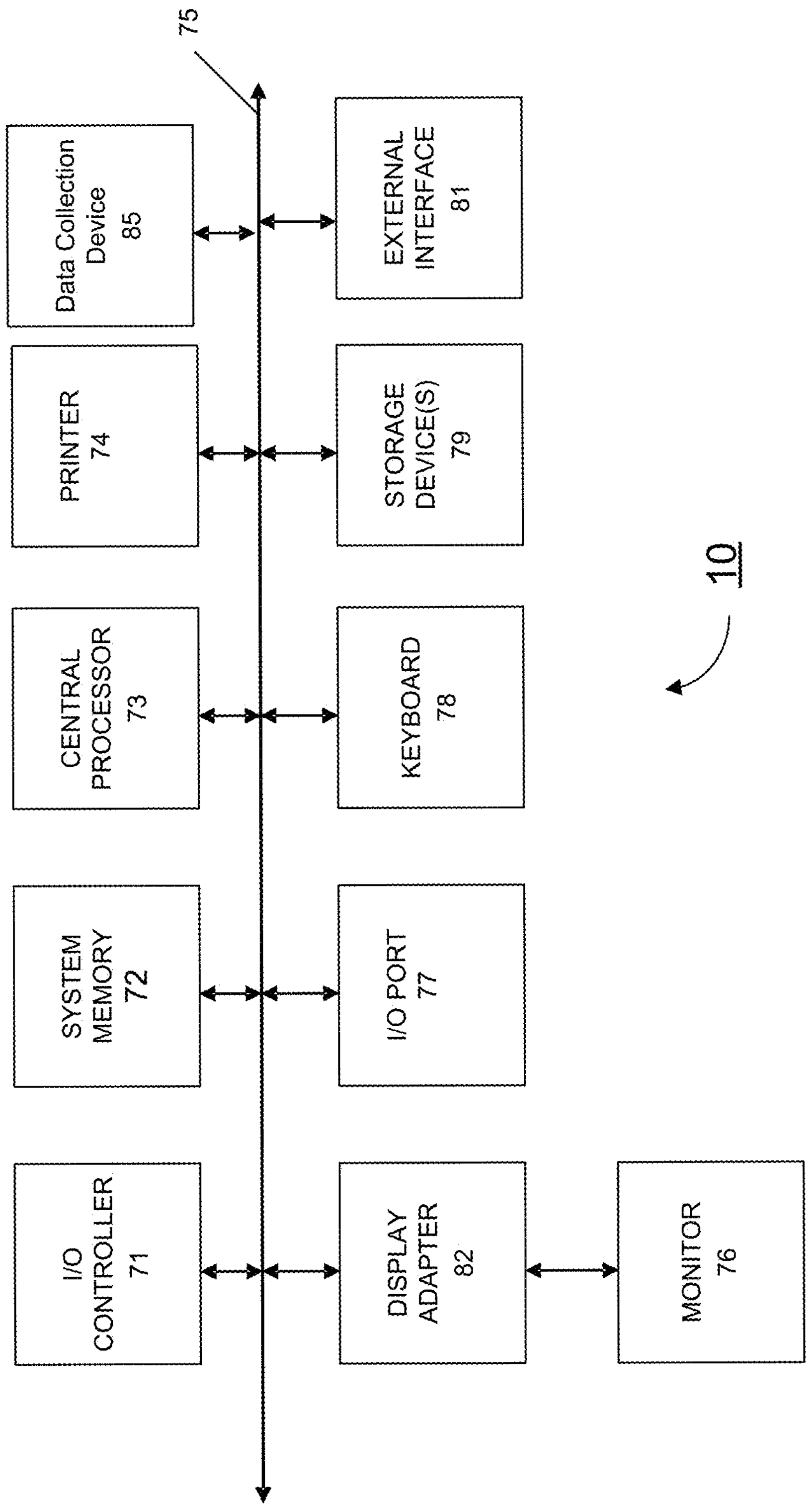
FIG. 9 illustrates an example computer system that may be utilized to implement techniques disclosed herein.

Any of the computer systems mentioned herein may utilize any suitable number of subsystems. Examples of such subsystems are shown in FIG. 9 in the computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones, and other mobile devices. In some embodiments, a cloud infrastructure (e.g., Amazon Web Services), a graphical processing unit (GPU), etc., can be used to implement the disclosed techniques.

The subsystems shown in FIG. 9 are interconnected via a system bus 75. Additional subsystems, such as a printer 74, keyboard 78, storage device(s) 79, monitor 76, which is coupled to display adapter 82, and others, are shown. Peripherals and input/output (I/O) devices, which couple to I/O controller 71, can be connected to the computer system by any number of means known in the art such as input/output (I/O) port 77 (e.g., USB, FireWire®). For example, I/O port 77 or external interface 81 (e.g. Ethernet, Wi-Fi) can be used to connect the computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer-readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystems, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C #, Objective-C, Swift, or scripting language such as Perl or Python using, for example, conventional or object-oriented techniques. The software code may be stored as a series of instructions or commands on a computer-readable medium for storage and/or transmission. A suitable non-transitory computer-readable medium can include random access memory (RAM), a read-only memory (ROM), a magnetic medium, such as a hard-drive or a floppy disk, or an optical medium such as a compact disk (CD) or DVD (digital versatile disk), flash memory, and the like. The computer-readable medium may be any combination of such storage or transmission devices.

Such programs may also be encoded and transmitted using carrier signals adapted for transmission via wired, optical, and/or wireless networks conforming to a variety of protocols, including the Internet. As such, a computer-readable medium may be created using a data signal encoded with such programs. Computer-readable media encoded with the program code may be packaged with a compatible device or provided separately from other devices (e.g., via Internet download). Any such computer-readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective step or a respective group of steps. Although presented as numbered steps, steps of methods herein can be performed at the same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a," "an," or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover, reference to a "first" or a "second" component does not limit the referenced component to a particular location unless expressly stated. The term "based on" is intended to mean "based at least in part on."

All patents, patent applications, publications, and descriptions mentioned herein are incorporated by reference in their entirety for all purposes. None is admitted to be prior art.

What is claimed is:

1. A computer implemented method, comprising:

receiving a file containing clinical data;

extracting input text strings from the file containing the clinical data;

detecting, using a natural language processing (NLP) model, entities from the input text strings, each entity including a label and a value, wherein the NLP model comprises a baseline NLP sub-model and a second NLP sub-model, the baseline NLP sub-model trained based on first training text strings from generic medical references and the second NLP sub-model trained based on second training text strings from clinical data records;

extracting, using the NLP model, values of the entities from the input text strings;

converting, based on a mapping table that maps entities and values to pre-determined terminologies, the values of at least some of the entities to corresponding pre-determined terminologies; and generating post-processed clinical data including the entities detected from the input text strings and the corresponding pre-determined terminologies.

2. The method of claim 1, wherein the NLP model comprises a graph comprising nodes and edges;

wherein each node corresponds to a text string;

wherein an edge between two nodes indicate a sequential relationship between two text strings represented by the two nodes; and wherein detecting the entities includes matching a sequence of text strings of the input text strings with a sequence of text strings represented in the graph.

3. The method of claim 2, further comprising: updating the graph based on training text strings that are tagged with names of entities.

4. The method of claim 1, wherein the NLP model wherein the input text strings are first input text strings; and wherein parameters of the NLP model are determined based on an accuracy of recognizing entities from second input text strings by the NLP model.

5. The method of claim 1 wherein parameters of the NLP model are based on inputting a sequence of text strings with a particular label into the NLP model and determining whether the NLP model correctly extracts entity/value pairs and/or correct context information.

6. The method of claim 5 wherein parameters of the NLP model are modified in response to determining that the NLP model incorrectly extracts entity/value pairs and/or context information, wherein the parameters are modified by at least one of adding a new terminology to the NLP model or new relationship between entities of the NLP model.

7. The method of claim 1, wherein multiple entities are recognized from a set of adjacent text strings of the input text string.

8. The method of claim 1, wherein standard terminologies are based on a Systematized Nomenclature of Medicine (SNOMED) standard; and wherein the standard terminologies comprise at least one of: SNOMED concepts, or SNOMED concept identifiers (ID).

9. The method of claim 1, further comprising: providing structured medical data from the post-processed clinical data to at least one of: a clinical decision support tool, a medical personnel portal, or a searchable medical database.

10. The method of claim 1, wherein the file comprises an image and wherein extracting input text strings from the file comprises an image recognition operation including at least one of: an optical character recognition (OCR) process, or an optical word recognition process.

11. The method of claim 1, wherein extracting input text strings comprises determining locations of the input text strings in the file; and wherein the method further comprises:

displaying, in a display interface, a representation of the file;

displaying, based on the determined locations of the input text strings, highlight markups from the post-processed clinical data over a subset of the input text strings for which entities are detected;

detecting a selection of at least one of the highlight markups; and responsive to detecting the selection, displaying a pop up window over the selected highlight markups, the pop up window including standard terminology of the entity detected from the input text string of the selected highlight markup.

12. The method of claim 1, wherein the file is received from one or more sources comprising at least one of: an EMR (electronic medical record) database, a PACS (picture archiving and communication system), a Digital Pathology (DP) system, an LIS (laboratory information system), an RIS (radiology information system), patient reported outcomes database, a wearable device, or a social media website.

13. A system comprising:

one or more processors; and a non-transitory computer-readable medium storing a plurality of instructions executable by the one or more processors to perform a method comprising:

receiving a file containing clinical data;

detecting, using a natural language processing (NLP) model, entities from input text strings, each entity including a label and a value, wherein the NLP model comprises a baseline NLP sub-model and a second NLP sub-model, the baseline NLP sub-model trained based on first training text strings from generic medical references and the second NLP sub-model trained based on second training text strings from clinical data records;

extracting, using the NLP model, values of the entities from the input text strings;

converting, based on a mapping table that maps entities and values to pre-determined terminologies, the values of at least some of the entities to corresponding pre-determined terminologies; and generating post-processed clinical data including the entities detected from the input text strings and the corresponding pre-determined terminologies.

14. The system of claim 13, wherein the NLP model comprises a graph comprising nodes and edges;

wherein each node corresponds to a text string;

wherein an edge between two nodes indicate a sequential relationship between two text strings represented by the two nodes; and wherein detecting the entities includes matching a sequence of text strings of the input text strings with a sequence of text strings represented in the graph.

15. The system of claim 13, wherein the input text strings are first input text strings; and wherein parameters of the NLP model are determined based on an accuracy of recognizing entities from second input text strings by the NLP model.

16. The system of claim 13 wherein parameters of the NLP model are modified in response to determining that the NLP model incorrectly extracts entity/value pairs and/or context information, wherein the parameters of the NLP model are modified by at least one of adding a new terminology to the NLP model or adding a relationship between entities of the NLP model.

17. A computer implemented method, comprising:

receiving a file containing clinical data;

extracting input text strings from the file containing the clinical data;

detecting, using a natural language processing (NLP) model, entities from the input text strings, each entity including a label and a value;

extracting, using the NLP model, values of the entities from the input text strings;

converting, based on a mapping table that maps the entities and values to pre-determined terminologies, the values of at least some of the entities to corresponding pre-determined terminologies; and generating post-processed clinical data including the entities detected from the input text strings and the corresponding pre-determined terminologies, wherein the input text strings are first input text strings; and wherein parameters of the NLP model are determined based on an accuracy of recognizing entities from second input text strings by the NLP model.

18. The method of claim 17, wherein the NLP model comprises a graph comprising nodes and edges;

wherein each node corresponds to a text string;

wherein an edge between two nodes indicate a sequential relationship between two text strings represented by the two nodes; and wherein detecting the entities includes matching a sequence of text strings of the input text strings with a sequence of text strings represented in the graph.

19. The method of claim 17, wherein the NLP model comprises a baseline NLP sub-model and a second NLP sub-model;

wherein the baseline NLP sub-model is trained based on first training text strings from generic medical documents; and wherein the second NLP sub-model is trained based on second training text strings from clinical data records.

20. The method of claim 17 wherein the parameters of the NLP model are modified in response to determining that the NLP model incorrectly extracts entity/value pairs and/or context information, wherein the parameters of the NLP model are modified by at least one of adding a new terminology to the NLP model or adding a relationship between entities of the NLP model.

* * * * *